US012582668B2

(12) United States Patent
Given et al.

(10) Patent No.: US 12,582,668 B2
(45) Date of Patent: Mar. 24, 2026

(54) METHODS FOR THE TREATMENT OF ALPHA-1 ANTITRYPSIN DEFICIENCY (AATD)

(71) Applicant: Arrowhead Pharmaceuticals, Inc., Pasadena, CA (US)

(72) Inventors: Bruce Given, Charleston, SC (US); Dawn Christianson, Solana Beach, CA (US); James C. Hamilton, Arcadia, CA (US); Zhen Li, San Diego, CA (US); Rui Zhu, San Diego, CA (US); Christine I. Wooddell, Madison, WI (US); Tao Pei, Middleton, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 1051 days.

(21) Appl. No.: 17/616,292

(22) PCT Filed: Jun. 5, 2020

(86) PCT No.: PCT/US2020/036359

§ 371 (c)(1),
(2) Date: Dec. 3, 2021

(87) PCT Pub. No.: WO2020/247774

PCT Pub. Date: Dec. 10, 2020

(65) Prior Publication Data

US 2022/0305046 A1 Sep. 29, 2022

Related U.S. Application Data

(60) Provisional application No. 62/858,059, filed on Jun. 6, 2019.

(51) Int. Cl.

| | |
|---|---|
| ***A61K 31/713*** | (2006.01) |
| ***A61K 45/06*** | (2006.01) |
| ***A61P 1/16*** | (2006.01) |

(52) U.S. Cl.

CPC ............ *A61K 31/713* (2013.01); *A61K 45/06* (2013.01); *A61P 1/16* (2018.01)

(58) Field of Classification Search

CPC .... A61K 31/713; A61K 9/0019; A61K 48/00; C12N 15/113; C12N 2310/346; C12N 2310/315

USPC ..................... 435/6.1, 91.1, 91.31, 455, 458; 514/44 A; 536/23.1, 24.5

See application file for complete search history.

(56) References Cited

U.S. PATENT DOCUMENTS

| | | | |
|---|---|---|---|
| 3,687,808 | A | 8/1972 | Merigan et al. |
| 5,034,506 | A | 7/1991 | Summerton et al. |
| 5,134,066 | A | 7/1992 | Rogers et al. |
| 5,212,295 | A | 5/1993 | Cook |
| 5,359,044 | A | 10/1994 | Cook et al. |
| 5,459,255 | A | 10/1995 | Cook et al. |
| 5,466,786 | A | 11/1995 | Buhr et al. |
| 5,489,677 | A | 2/1996 | Sanghvi et al. |
| 5,519,134 | A | 5/1996 | Acevedo et al. |
| 5,521,302 | A | 5/1996 | Cook |
| 5,539,082 | A | 7/1996 | Nielson et al. |
| 5,552,540 | A | 9/1996 | Haralambidis |
| 5,587,361 | A | 12/1996 | Cook et al. |
| 5,591,722 | A | 1/1997 | Montgomery et al. |
| 5,594,121 | A | 1/1997 | Froehler et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,646,265 | A | 7/1997 | McGee |
| 5,700,920 | A | 12/1997 | Altmann et al. |
| 5,885,968 | A | 3/1999 | Biessen et al. |
| 6,172,209 | B1 | 1/2001 | Manoharan et al. |
| 6,268,490 | B1 | 7/2001 | Imanishi et al. |
| 6,271,358 | B1 | 8/2001 | Manoharan et al. |
| 7,056,704 | B2 | 6/2006 | Tuschl et al. |
| 7,335,765 | B2 | 2/2008 | Kaneko et al. |
| 7,691,997 | B2 | 4/2010 | Khvorova et al. |
| 8,084,599 | B2 | 12/2011 | Rossi et al. |
| 8,349,809 | B2 | 1/2013 | Brown |
| 8,394,628 | B2 | 3/2013 | Tuschl et al. |
| 8,513,207 | B2 | 8/2013 | Brown |
| 8,648,185 | B2 | 2/2014 | Mcswigen et al. |

(Continued)

FOREIGN PATENT DOCUMENTS

| | | | |
|---|---|---|---|
| CN | 103547272 | A | 1/2014 |
| CN | 106535917 | A | 3/2017 |

(Continued)

OTHER PUBLICATIONS

International Search Report and Written Opinion for Application No. PCT/US2020/036359 mailed Sep. 30, 2020.

(Continued)

*Primary Examiner* — Jane J Zara

(74) *Attorney, Agent, or Firm* — Wolf, Greenfield & Sacks, P.C.

(57) ABSTRACT

Described are methods for treating alpha-1 antitrypsin deficiency (AATD) in a human patient in need of treatment, using pharmaceutical compositions that include AAT RNAi agents. The pharmaceutical compositions disclosed herein that include AAT RNAi agents, when administered to a human patient in need thereof, treat liver diseases associated with AAT deficiency such as chronic hepatitis, cirrhosis, increased risk of hepatocellular carcinoma, transaminitis, cholestasis, fibrosis, fulminant hepatic failure, and other liver-related diseases.

22 Claims, 16 Drawing Sheets

Specification includes a Sequence Listing.

(56) References Cited

U.S. PATENT DOCUMENTS

| | | | | |
|---|---|---|---|---|
| 9,340,784 | B2 | 5/2016 | Monia et al. | |
| 9,458,457 | B2 | 10/2016 | Brown et al. | |
| 9,879,261 | B2 | 1/2018 | Brown et al. | |
| 10,006,025 | B2 | 6/2018 | Wooddell et al. | |
| 10,450,565 | B2 * | 10/2019 | Li | A61K 31/713 |
| 11,203,756 | B2 * | 12/2021 | Li | A61P 1/16 |
| 11,384,355 | B2 | 7/2022 | Wooddell et al. | |
| 11,884,920 | B2 | 1/2024 | Li et al. | |
| 12,188,017 | B2 | 1/2025 | Wooddell et al. | |
| 2005/0137153 | A1 | 6/2005 | Mcswiggen et al. | |
| 2006/0234247 | A1 | 10/2006 | Puttaraju et al. | |
| 2007/0253936 | A1 | 11/2007 | Kay et al. | |
| 2009/0029931 | A1 | 1/2009 | Tachas et al. | |
| 2009/0247608 | A1 | 10/2009 | Manoharan et al. | |
| 2010/0048680 | A1 | 2/2010 | Liu et al. | |
| 2010/0056768 | A1 | 3/2010 | Wengel | |
| 2011/0028531 | A1 | 2/2011 | Feinstein et al. | |
| 2011/0207799 | A1 | 8/2011 | Rozema et al. | |
| 2013/0190484 | A1 | 7/2013 | Rozema et al. | |
| 2013/0281658 | A1 | 10/2013 | Rozema et al. | |
| 2014/0235693 | A1 | 8/2014 | Sehgal et al. | |
| 2014/0350071 | A1 | 11/2014 | Sehgal et al. | |
| 2015/0011607 | A1 | 1/2015 | Brown et al. | |
| 2015/0361427 | A1 | 12/2015 | Wooddell et al. | |
| 2016/0244752 | A1 | 8/2016 | Sehgal et al. | |
| 2017/0035796 | A1 | 2/2017 | Wooddell et al. | |
| 2017/0130221 | A1 | 5/2017 | Brown et al. | |
| 2017/0253875 | A1 | 9/2017 | Rozema et al. | |
| 2018/0064819 | A1 | 3/2018 | Li et al. | |
| 2018/0195069 | A1 | 7/2018 | Li et al. | |
| 2018/0258430 | A1 | 9/2018 | Wooddell et al. | |
| 2019/0071670 | A1 | 3/2019 | Wooddell et al. | |
| 2019/0284558 | A1 | 9/2019 | Wooddell et al. | |
| 2020/0208149 | A1 | 7/2020 | Li et al. | |
| 2022/0170015 | A1 | 6/2022 | Li et al. | |
| 2023/0002768 | A1 | 1/2023 | Wooddell et al. | |
| 2023/0348905 | A1 | 11/2023 | Christianson et al. | |
| 2024/0141351 | A1 | 5/2024 | Li et al. | |
| 2025/0197861 | A1 | 6/2025 | Wooddell et al. | |

FOREIGN PATENT DOCUMENTS

| | | | |
|---|---|---|---|
| JP | 2008-516991 | A | 5/2008 |
| JP | 2013-539967 | A | 10/2013 |
| JP | 2016-520312 | A | 7/2016 |
| JP | 2020-503070 | A | 1/2020 |
| WO | WO 1993/007883 | A1 | 4/1993 |
| WO | WO 1997/044348 | A1 | 11/1997 |
| WO | WO 1999/014226 | A2 | 3/1999 |
| WO | WO 1999/038987 | A1 | 8/1999 |
| WO | WO 2000/053722 | A2 | 9/2000 |
| WO | WO 2004/045543 | A2 | 6/2004 |
| WO | WO 2004/083430 | A1 | 9/2004 |
| WO | WO 2006/086821 | A1 | 8/2006 |
| WO | WO 2008/016391 | A2 | 2/2008 |
| WO | WO 2008/022309 | A2 | 2/2008 |
| WO | WO 2011/104169 | A1 | 9/2011 |
| WO | WO 2012/033848 | A1 | 3/2012 |
| WO | WO 2012/083185 | A2 | 6/2012 |
| WO | WO 2012/178033 | A2 | 12/2012 |
| WO | WO 2013/032829 | A1 | 3/2013 |
| WO | WO 2013/142514 | A1 | 9/2013 |
| WO | WO 2013/158141 | A1 | 10/2013 |
| WO | WO 2014/190137 | A1 | 11/2014 |
| WO | WO 2014/197524 | A2 | 12/2014 |
| WO | WO 2015/003113 | A2 | 1/2015 |
| WO | WO 2015/188197 | A2 | 12/2015 |
| WO | WO 2015/195628 | A2 | 12/2015 |
| WO | WO 2017/139616 | A1 | 8/2017 |
| WO | WO 2017/156012 | A1 | 9/2017 |
| WO | WO 2017/214518 | A1 | 12/2017 |
| WO | WO 2018/098117 | A1 | 5/2018 |
| WO | WO 2018/132432 | A1 | 7/2018 |
| WO | WO 2018/236273 | A1 | 12/2018 |
| WO | WO 2020/247774 | A1 | 12/2020 |

OTHER PUBLICATIONS

International Preliminary Report on Patentability for Application No. PCT/US2020/036359 mailed Dec. 16, 2021.

Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.

American Thoracic Society, American Thoracic Society/European Respiratory Society statement: standards for the diagnosis and management of individuals with alpha-1 antitrypsin deficiency. Am J Respir Crit Care Med. Oct. 1, 2003;168(7):818-900. doi: 10.1164/rccm.168.7.818.

Baenziger et al., Galactose and N-Acetylgalactosamine-Specific Endocytosis of Glycopeptides by Isolated Rat Hepatocytes. Cell. Nov. 1980;22(2 Pt 2):611-20. doi: 10.1016/0092-8674(80)90371-2.

Bals, Alpha-1-antitrypsin deficiency. Best Pract Res Clin Gastroenterol. Oct. 2010;24(5):629-33. doi: 10.1016/j.bpg.2010.08.006.

Biessen et al., Synthesis of cluster galactosides with high affinity for the hepatic asialoglycoprotein receptor. J Med Chem. Apr. 28, 1995;38(9):1538-46. doi: 10.1021/jm00009a014.

Bondensgaard et al., Structural studies of LNA:RNA duplexes by NMR: conformations and implications for RNase H activity. Chemistry. Aug. 4, 2000;6(15):2687-95. doi: 10.1002/1521-3765(20000804)6:15<2687::aid-chem2687>3.0.co;2-u.

Braasch et al., Locked nucleic acid (LNA): fine-tuning the recognition of DNA and RNA. Chem Biol. Jan. 2001;8(1):1-7. doi: 10.1016/s1074-5521(00)00058-2.

Carlson et al., Accumulation of PiZ alpha 1-antitrypsin causes liver damage in transgenic mice. J Clin Invest. Apr. 1989;83(4):1183-90. doi: 10.1172/JCI113999.

Carrell et al., Alpha1-antitrypsin deficiency—a model for conformational diseases. N Engl J Med. Jan. 3, 2002;346(1):45-53. doi: 10.1056/NEJMra010772.

Cichy et al., Biosynthesis of alpha1-proteinase inhibitor by human lung-derived epithelial cells. J Biol Chem. Mar. 28, 1997;272(13):8250-5. doi: 10.1074/jbc.272.13.8250.

Cohen, Interrelationships between the human alveolar macrophage and alpha-1-antitrypsin. J Clin Invest. Nov. 1973;52(11):2793-9. doi: 10.1172/JCI107475.

Connolly et al., Binding and endocytosis of cluster glycosides by rabbit hepatocytes. Evidence for a short-circuit pathway that does not lead to degradation. J Biol Chem. Jan. 25, 1982;257(2):939-45.

Cook, Medicinal Chemistry of Antisense Oligonucleotides-Future Opportunities. Anti-Cancer Drug Des. Dec. 1991;6(6):585-607.

Crinelli et al., Design and characterization of decoy oligonucleotides containing locked nucleic acids. Nucleic Acids Res. Jun. 1, 2002;30(11):2435-43. doi: 10.1093/nar/30.11.2435.

Crooke et al., Pharmacokinetic properties of several novel oligonucleotide analogs in mice. J Pharmacol Exp Ther. May 1996;277(2):923-37.

Cruz et al., In vivo post-transcriptional gene silencing of alpha-1 antitrypsin by adeno-associated virus vectors expressing siRNA. Lab Invest. Sep. 2007;87(9):893-902. doi: 10.1038/labinvest.3700629. Epub Jun. 25, 2007.

Cruz et al., Post-Transcriptional Gene Silencing of Alpha-I Antitrypsin by Small Interfering RNAs (siRNA). Mol Ther. 2006; 13(1):S45-S46.

Czauderna et al., Structural variations and stabilising modifications of synthetic siRNAs in mammalian cells. Nucleic Acids Res. Jun. 1, 2003;31(11):2705-16. doi: 10.1093/nar/gkg393.

De Serres et al., Prevalence of al-antitrypsin deficiency alleles PI*S and PI*Z worldwide and effective screening for each of the five phenotypic classes PI*MS, PI*MZ, PI*SS, PI*SZ, and PI*ZZ: a comprehensive review. Ther Adv Respir Dis. Oct. 2012;6(5):277-95. doi: 10.1177/1753465812457113. Epub Aug. 29, 2012.

Delgado et al., The Uses and Properties of PEG-Linked Proteins. Crit Rev Ther Drug Carrier Syst. 1992;9(3-4):249-304.

Elmen et al., Locked nucleic acid (LNA) mediated improvements in siRNA stability and functionality. Nucleic Acids Res. Jan. 14, 2005;33(1):439-47. doi: 10.1093/nar/gki193. Print 2005.

Elzouki et al., Risk of hepatobiliary disease in adults with severe alpha 1-antitrypsin deficiency (PiZZ): is chronic viral hepatitis B or C an additional risk factor for cirrhosis and hepatocellular carci-

(56) References Cited

OTHER PUBLICATIONS noma? Eur J Gastroenterol Hepatol. Oct. 1996;8(10):989-94. doi: 10.1097/00042737-199610000-00010.
Eriksson, Alpha-1-antitrypsin deficiency: natural course and therapeutic strategies. Falk Symposium 115: Liver cirrhosis and its development. 2001; 307-15.
Feldmann et al., The ultrastructure of hepatocytes in alpha-1-antitrypsin deficiency with the genotype Pi--. Gut. Oct. 1975;16(10):796-9. doi: 10.1136/gut.16.10.796.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Greene et al., Z α-1 antitrypsin deficiency and the endoplasmic reticulum stress response. World J Gastrointest Pharmacol Ther. Oct. 6, 2010;1(5):94-101. doi: 10.4292/wjgpt.v1.i5.94.
Grimm et al., Fatality in mice due to oversaturation of cellular microRNA/short haiipin RNA Pathways. Nature. May 25, 2006;441(7092):537-41. doi: 10.1038/nature04791.
Guo et al., Antisense oligonucleotide treatment ameliorates alpha-1 antitrypsin-related liver disease in mice. J Clin Invest. Jan. 2014;124(1):251-61. doi: 10.1172/JCI67968. Epub Dec. 20, 2013.
Guzaev et al., A conformationally preorganized universal solid support for efficient oligonucleotide synthesis. J Am Chem Soc. Mar. 5, 2003;125(9):2380-1. doi: 10.1021/ja0284613.
Hamm et al., Incorporation of 2'-Deoxy-2'-mercaptocytidine into Oligonucleotides via Phosphoramidite Chemistry. J Org Chem. May 16, 1997;62(10):3415-3420. doi: 10.1021/jo9700960.
Hunt et al., Alpha 1 anti-trypsin: one protein, many functions. Curr Mol Med. Aug. 2012;12(7):827-35. doi: 10.2174/156652412801318755.
Iobst et al., Selective sugar binding to the carbohydrate recognition domains of the rat hepatic and macrophage asialoglycoprotein receptors. J Biol Chem. Mar. 22, 1996;271(12):6686-93. doi: 10.1074/jbc.271.12.6686.
Joshi et al., siRNA: novel therapeutics from functional genomics. Biotechnol Genet Eng Rev. Oct. 2014;30(1-2):1-30. doi: 10.1080/02648725.2014.921495.
Kabanov et al., A new class of antivirals; antisense oligonucleotides combined with a hydrophobic substituent effectively inhibit influenza virus reproduction and synthesis of virus-specific proteins in MDCK cells. FEBS Lett. Jan. 1, 1990;259(2):327-30. doi: 10.1016/0014-5793(90)80039-1.
Kamola et al., The siRNA Non-seed Region and Its Target Sequences are Auxiliary Determinants of Off-Target Effects. PLoS Comput Biol. Dec. 11, 2015;11(12):e1004656. doi: 10.1371/journal.pcbi.1004656. eCollection Dec. 2015.
Kemmer et al., Alpha-1-antitrypsin deficiency: outcomes after liver transplantation. Transplant Proc. Jun. 2008;40(5):1492-4. doi: 10.1016/j.transproceed.2008.02.075.
Kok et al., Prevalence of genetic polymorphisms in the promoter region of the alpha-1 antitrypsin (SERPINA1) gene in chronic liver disease: a case control study. BMC Gastroenterology. Feb. 20, 2010;10:22. doi: 10.1186/1471-230X-10-22.
Kurreck et al., Design of Antisense Oligonucleotides Stabilized by Locked Nucleic Acids. Nucleic Acids Res. May 1, 2002;30(9):1911-8. doi: 10.1093/nar/30.9.1911.
Letsinger et al., Cholesteryl-conjugated oligonucleotides: synthesis, properties, and activity as inhibitors of replication of human immunodeficiency virus in cell culture. Proc Natl Acad Sci USA. Sep. 1989;86(17):6553-6. doi: 10.1073/pnas.86.17.6553.
Li et al., Combination Therapy Utilizing shRNA and Optimize Alpha-I Antitrypsin (AAT) Expression Cassette for Treatment and Correction of AAT Liver Deficiency. Mol Ther. 2009; 17(1):S12.
Lindblad et al., Alpha-1-antitrypsin mutant Z protein content in individual hepatocytes correlates with cell death in a mouse model. Hepatology. Oct. 2007;46(4):1228-35. doi: 10.1002/hep.21822.
Lomas et al., The mechanism of Z alpha 1-antitrypsin accumulation in the liver. Nature. Jun. 18, 1992;357(6379):605-7. doi: 10.1038/357605a0.
Long et al., Complete sequence of the cDNA for human alpha 1-antitrypsin and the gene for the S variant. Biochemistry. Oct. 9, 1984;23(21):4828-37. doi: 10.1021/bi00316a003.
Manoharan et al., Lipidic Nucleic Acids. Tetrahedron Letters. 1995; 36: 3651-4.
McLean et al., Gene targeted therapeutics for liver disease in alpha-I antitrypsin deficiency. Biologics. 2009;3:63-75. Epub Jul. 13, 2009.
Mishra et al., Improved leishmanicidal effect of phosphorothioate antisense oligonucleotides by LDL-mediated delivery. Biochim Biophys Acta. Nov. 7, 1995;1264(2):229-37. doi: 10.1016/0167-4781(95)00145-7.
Mueller et al., Development of Simultaneous Gene Augmentation and Reduction of Mutant Gene Expression with a Single Recombinant AA V for Alpha One Antitrypsin Disease. Mol Ther. 2009; 17(1): S391-S392.
Mueller et al., In Vivo Allele Specific Knockdown of Mutant Alpha One Antitrypsin using Recombinant AA V Delivered shRNA. Mol Ther. 2009; 17(1): S313.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. doi: 10.1038/mt.2011.292. Epub Jan. 17, 2012.
Nelson et al., Diagnosis and management of patients with α1-antitrypsin (A1AT) deficiency. Clin Gastroenterol Hepatol. Jun. 2012;10(6):575-80. doi: 10.1016/j.cgh.2011.12.028. Epub Dec. 23, 2011.
Nielsen et al., Incorporation of (R)- and (S)-3',4'-seco-thymidine into oligodeoxynucleotides: hybridization properties and enzymatic stability. Nucleic Acids Res. Mar. 11, 1994;22(5):703-10. doi: 10.1093/nar/22.5.703.
Nielsen et al., Synthesis and evaluation of oligodeoxynucleotides containing acyclic nucleosides: introduction of three novel analogues and a summary. Bioorg Med Chem. Jan. 1995;3(1):19-28. doi: 10.1016/0968-0896(94)00143-q.
Paakko et al., Activated neutrophils secrete stored alpha 1-antitrypsin. Am J Respir Crit Care Med. Dec. 1996;154(6 Pt 1):1829-33. doi: 10.1164/ajrccm.154.6.8970377.
Perlmutter et al., Hepatic fibrosis and carcinogenesis in α1-antitrypsin deficiency: a prototype for chronic tissue damage in gain-of-function disorders. Cold Spring Harb Perspect Biol. Mar. 1, 2011;3(3):a005801. doi: 10.1101/cshperspect.a005801.
Perlmutter, Alpha-1-antitrypsin deficiency: importance of proteasomal and autophagic degradative pathways in disposal of liver disease-associated protein aggregates. Annu Rev Med. 2011;62:333-45. doi: 10.1146/annurev-med-042409-151920.
Propst et al., Prevalence of hepatocellular carcinoma in alpha-1-antitrypsin deficiency. J Hepatol. Dec. 1994;21(6):1006-11. doi: 10.1016/s0168-8278(05)80609-9.
Saison-Behmoaras et al., Short Modified Antisense Oligonucleotides Directed Against Ha-ras Point Mutation Induce Selective Cleavage of the mRNA and Inhibit T24 Cells Proliferation. Embo J. May 1991;10(5):1111-8.
Sehgal et al., Developing an RNAi Therapeutic for Liver Disease Associated With Alpha-1-Antitrypsin Deficiency. AASLD Abstracts. Oct. 2013. 58(4): 412A-14.
Shea et al., Synthesis, hybridization properties and antiviral activity of lipid-oligodeoxynucleotide conjugates. Nucleic Acids Res. Jul. 11, 1990;18(13):3777-83. doi: 10.1093/nar/18.13.3777.
Song et al., Crystal structure of an uncleaved alpha 1-antitrypsin reveals the conformation of its inhibitory reactive loop. FEBS Lett. Dec. 18, 1995;377(2):150-4. doi: 10.1016/0014-5793(95)01331-8.
Stoller et al., A review of al-antitrypsin deficiency. Am J Respir Crit Care Med. Feb. 1, 2012;185(3):246-59. doi: 10.1164/rccm.201108-1428CI. Epub Sep. 29, 2011.
Sveger, Liver disease in alpha1-antitrypsin deficiency detected by screening of 200,000 infants. N Engl J Med. Jun. 10, 1976;294(24):1316-21. doi: 10.1056/NEJM197606102942404.
Svinarchuk et al., Inhibition of HIV proliferation in MT-4 cells by antisense oligonucleotide conjugated to lipophilic groups. Biochimie. 1993;75(1-2):49-54. doi: 10.1016/0300-9084(93)90024-m.
Teckman et al., Advances in alpha-1-antitrypsin deficiency liver disease. Curr Gastroenterol Rep. Jan. 2014;16(1):367. doi: 10.1007/s11894-013-0367-8.

(56) References Cited

OTHER PUBLICATIONS

Teckman et al., Mitochondrial autophagy and injury in the liver in alpha 1-antitrypsin deficiency. Am J Physiol Gastrointest Liver Physiol. May 2004;286(5):G851-62. doi: 10.1152/ajpgi.00175.2003. Epub Dec. 18, 2003.

Teckman, Liver disease in alpha-1 antitrypsin deficiency: current understanding and future therapy. COPD. Mar. 2013;10 Suppl 1:35-43. doi: 10.3109/15412555.2013.765839.

Thomson et al., Synthesis and Properties of Diuridine Phosphate Analogues Containing Thio and Amino Modifications. J Org Chem. Sep. 6, 1996;61(18):6273-6281. doi: 10.1021/jo9607951.

Venembre et al., Secretion of alpha 1-antitrypsin by alveolar epithelial cells. FEBS Lett. Jun. 13, 1994;346(2-3):171-4. doi: 10.1016/0014-5793(94)80695-0.

Wagner, The state of the art in antisense research. Nat Med. Nov. 1995;1(11):1116-8. doi: 10.1038/nm1195-1116.

Wahlestedt et al., Potent and nontoxic antisense oligonucleotides containing locked nucleic acids. Proc Natl Acad Sci U S A. May 9, 2000;97(10):5633-8. doi: 10.1073/pnas.97.10.5633.

Extended European Search Report for Application No. 20818171.9, mailed Oct. 2, 2023.

Geary et al., Effect of dose and plasma concentration on liver uptake and pharmacologic activity of a 2'-methoxyethyl modified chimeric antisense oligonucleotide targeting PTEN. Biochem Pharmacol. Aug. 1, 2009;78(3):284-91. doi: 10.1016/j.bcp.2009.04.013. Epub Apr. 22, 2009.

Turner et al., Hepatic-targeted RNA interference provides robust and persistent knockdown of alpha-1 antitrypsin levels in ZZ patients. J Hepatol. Aug. 2018;69(2):378-384. doi: 10.1016/j.jhep.2018.03.012. Epub Mar. 21, 2018.

Yamansarov et al., Low molecular weight glycoconjugates of the antiviral drug ribavirin with galactosamine derivatives—a new approach to targeted therapy of liver diseases. Russian Biotherapeutic Journal, Special Issue: Proceedings of the conference "Domestic antitumor drugs". 2017; 16(S1): 86-87.

* cited by examiner

| Single Dose Normal Healthy Volunteers (Cohorts 1, 2, 3, 4 are double blind; Cohorts 2b, 3b, 4b are open label) | | | Multi-dose Normal Healthy Volunteer (double blind) |
|---|---|---|---|
| Cohort | Dose (Day 1) | Day 15 safety evaluation | Dose Regimen |
| Cohort 1 | 35 mg | | N/A |
| Cohort 2/2b | 100 mg | | 100 mg dosed on Day 29, 57/ Cohort 2b: single dose only (Day 1) |
| Cohort 3/3b | 200 mg | | 200 mg dosed on Day 29, 57/ Cohort 3b: single dose only (Day 1) |
| Cohort 4/4b | 300 mg | | 300 mg dosed on Day 29, 57/ Cohort 4b: single dose only (Day 1) |

FIG. 4

METHODS FOR THE TREATMENT OF ALPHA-1 ANTITRYPSIN DEFICIENCY (AATD)

RELATED APPLICATIONS

This application is a national stage filing under 35 U.S.C. § 371 of International Application number PCT/US2020/036359, filed Jun. 5, 2020, which claims the benefit under 35 U.S.C. § 119(e) to U.S. Provisional Application No. 62/858,059, filed Jun. 6, 2019. The contents of each of these applications are incorporated herein by reference in their entirety.

SEQUENCE LISTING

The instant application contains a Sequence Listing which has been submitted in ASCII format via EFS-Web and is hereby incorporated by reference in its entirety. The ASCII copy, created on Dec. 3, 2021, is named T083370012US01-SEQ-ZJG.TXT and is 5,797 bytes in size.

FIELD OF THE INVENTION

Disclosed herein are methods for the treatment of alpha-1 antitrypsin deficiency (AATD) in a human subject, including treatment of the symptoms and diseases caused by AATD, using pharmaceutical compositions that include RNA interference (RNAi) agents that inhibit alpha-1 antitrypsin gene expression.

BACKGROUND

Alpha-1 antitrypsin (AAT, α1-antitrypsin, or A1AT) is a protease inhibitor belonging to the serpin superfamily encoded in humans by the SERPINA1 gene. Normal AAT protein is a circulating glycoprotein protease inhibitor primarily synthesized in the liver by hepatocytes and secreted into the blood. The known physiologic function of AAT is to inhibit neutrophil proteases, which serves to protect host tissues from non-specific injury during periods of inflammation.

Alpha-1 antitrypsin deficiency (AATD) is an autosomal, codominant genetic disorder that results in low circulating levels of AAT and causes early pulmonary disease in adults and liver disease in children and adults. The prevalence range of AAT deficiency (AATD) is about 1 in every 1,500 to 5.000 individuals and most often affects persons with European ancestry.

The most clinically significant form of AATD is caused by the Z mutation. The Z mutant allele, through a single point mutation, renders the mutant Z form AAT protein (the "Z-AAT protein") prone to abnormal folding causing intracellular retention in the endoplasmic reticulum (ER) of hepatocytes. Other rarer mutations also result in misfolded accumulated protein in hepatocytes. The mutant Z-AAT protein monomers are able to a mass into polymer aggregates, which are sometimes referred to as "globules." The polymeric globule masses stress the ER and trigger a cycle of continuous hepatocyte injury and healing, leading to fibrosis, cirrhosis, and increased risk of hepatocellular carcinoma. Further, the absence of circulating anti-protease activity leaves the lung vulnerable to injury by neutrophil elastase, particularly in the setting of lung inflammation, resulting in the development of respiratory complications such as emphysema or other pulmonary disease.

Individuals with the homozygous PiZZ genotype have severe deficiency of functional AAT. Weekly use of AAT augmentation therapy, using purified human AAT, helps prevent lung damage in affected individuals. Such currently marketed products include, for example, Prolastin®-C, Prolastin®, Glassian™, Aralast® NP, and Zemaira®. However, while the administration of purified AAT can ameliorate or help prevent lung damage caused by the absence or low levels of endogenously secreted AAT, AATD patients (with an AAT-mutation that results in polymer formation) remain vulnerable to endoplasmic reticulum liver storage disease caused by the deposition and accumulation of excessive abnormally folded AAT protein. Accumulated Z-AAT protein in a "globule" conformation in hepatocytes is a well-known histologic characteristic of AATD liver disease and is believed to lead to proteotoxic effects that are responsible for inducing liver injury, including liver cell damage and death and chronic liver injury in individuals with AATD (see, e.g., D. Lindblad et al., Hepatology 2007, 46: 1228-1235). It has been reported that null/null patients, who produce no AAT, develop severe pulmonary disease but have normal liver morphology, providing evidence that the accumulation of the mutant AAT, and not the lack of circulating AAT, leads to hepatic disease (Feldman, G. et al, *The Ultrastructure of Hepatocytes in alpha-*1 *antitrypsin deficiency with genotype Pi_*, *Gut.* 1975; 16:796-799).

AATD predisposes individuals to liver disease in children and adults and to early-onset emphysema in adults. Patients with AATD often develop liver disease, which can be severe or fatal, even in infancy. While some patients with AATD escape detection initially, eventually fibrosis accumulates and leads to clinically apparent liver disease. Clinical presentations of injury in the liver include chronic hepatitis, cirrhosis, increased risk of hepatocellular carcinoma, transaminitis, cholestasis, fibrosis, and even fulminant hepatic failure.

Z-AAT protein globule accumulation in hepatocytes has been clearly identified as the cause of progressive liver disease in AATD patients. Elimination of mutant protein accumulation in hepatocytes may halt the progression of liver disease. Removal of the mutant protein insult may also allow for regression of already present fibrosis. There is currently no clinically approved treatment to prevent the onset, slow the progression, or otherwise treat liver disease caused by AATD.

RNAi agents have emerged as a promising avenue for treating AATD patients. Dosing strategies are an important consideration in the treatment of AATD with RNAi agents. Less frequent dosing is valued by patients, leads to increased compliance, and smaller dosing amounts can be advantageous in the overall safety profile of the drug. There thus exists a need for a low dose, infrequent method for the treatment of AATD.

SUMMARY

Described herein are methods of treating alpha-1 antitrypsin deficiency (AATD) in a human subject in need thereof. In one aspect, the methods comprise administering to the human subject a pharmaceutical composition that includes the composition described in Table 2 (i.e., AAT RNAi Drug Substance, also referred to herein as ADS-001) at a dose of between about 5 mg and about 300 mg of the AAT RNAi Drug Substance, wherein the pharmaceutical composition is administered subcutaneously and there is at least about one month between doses (i.e., at least monthly dosing). In some embodiments, the pharmaceutical composition used in the methods disclosed herein comprises, consists of, or consists essentially of the Formulated AAT RNAi Drug Substance as described in Table 3 (also referred to herein as ADS-001-1).

Additionally, described herein are methods of treating AATD in a human subject in need thereof, the methods comprising administering to the human subject a pharmaceutical composition that includes the AAT RNAi Drug Substance as described in Table 2 (i.e., ADS-001) at a dose of between about 5 mg and about 200 mg, wherein the pharmaceutical composition is administered subcutaneously and there is at least about one month between dose administrations (i.e., monthly dosing).

Further described herein are methods of treating AATD in a human subject in need thereof, the methods comprising administering to the human subject a pharmaceutical composition that includes the AAT RNAi Drug Substance as described in Table 2 (i.e., ADS-001) at a dose of between about 5 mg and about 300 mg, wherein the pharmaceutical composition is administered subcutaneously and there is about three months between dose administrations (i.e., quarterly dosing).

Also described herein are methods of treating AATD in a human subject in need thereof, the methods comprising administering to the human subject a pharmaceutical composition that includes the AAT RNAi Drug Substance as described in Table 2 (i.e., ADS-001) at a dose of between about 5 mg and about 200 mg, wherein the pharmaceutical composition is administered subcutaneously and there is about three months between dose administrations (i.e., quarterly dosing).

Described herein are methods of treating AATD in a human subject in need thereof, the methods comprising administering to the human subject a pharmaceutical composition that includes the AAT RNAi Drug Substance as described in Table 2 (i.e., ADS-001) at a dose of between about 5 mg and about 300 mg, wherein the pharmaceutical composition is administered subcutaneously, and wherein the initial dose is followed by a second dose about one month later, and thereafter for subsequent doses there is about three months between dose administrations.

Described herein are methods of treating AATD in a human subject in need thereof, the methods comprising administering to the human subject a pharmaceutical composition that includes the AAT RNAi Drug Substance as described in Table 2 (i.e., ADS-001) at a dose of between about 5 mg and about 200 mg, wherein the pharmaceutical composition is administered subcutaneously, and wherein the initial dose is followed by a second dose about one month later, and thereafter for subsequent doses there is about three months between dose administrations.

In some embodiments, the dose of AAT RNAi Drug Substance administered in each dose is between about 25 mg and about 200 mg. In some embodiments, the dose of AAT RNAi Drug Substance administered in each dose is between about 100 mg and about 200 mg. In some embodiments, the dose of AAT RNAi Drug Substance administered in each dose is about 100 mg. In some embodiments, the dose of AAT RNAi Drug Substance administered in each dose is about 200 mg. In some embodiments, the dose of AAT RNAi Drug Substance administered in each dose is no greater than 200 mg.

The treatment methods disclosed herein can slow or halt the progression of liver disease in a human subject having AATD, which can allow for fibrotic tissue repair. The methods disclosed herein can, in some embodiments, treat AATD liver diseases including fibrosis, cirrhosis, increased risk of hepatocellular carcinoma, chronic hepatitis, transaminitis, cholestasis, fulminant hepatic failure, and other liver-related conditions and diseases caused by AATD.

The pharmaceutical compositions that include AAT RNAi agents disclosed herein can be administered to a human subject to inhibit the expression of the alpha-1 antitrypsin gene in the subject. In some embodiments, the subject is a human that has been previously diagnosed with having AATD.

Another aspect of the invention provides for the use of the AAT RNAi Drug Substance described in Table 2 for the treatment of alpha-1 antitrypsin deficiency (AATD) in a human subject in need thereof, wherein the use comprises administering to the patient a pharmaceutical composition that comprises the AAT RNAi Drug Substance described in Table 2 at a dose of between about 5 mg to about 300 mg of the AAT RNAi Drug Substance, wherein the pharmaceutical composition is administered once each month by subcutaneous injection.

Another aspect of the invention provides for the use of the AAT RNAi Drug Substance described in Table 2 for the treatment of alpha-1 antitrypsin deficiency (AATD) in a human subject in need thereof, wherein the use comprises administering to the patient a pharmaceutical composition that comprises the AAT RNAi Drug Substance described in Table 2 at a dose of between about 5 mg to about 300 mg of the AAT RNAi Drug Substance, wherein the pharmaceutical composition is administered once every three months by subcutaneous injection.

Other objects, features, aspects, and advantages of the invention will be apparent from the following detailed description, accompanying figures, and from the claims.

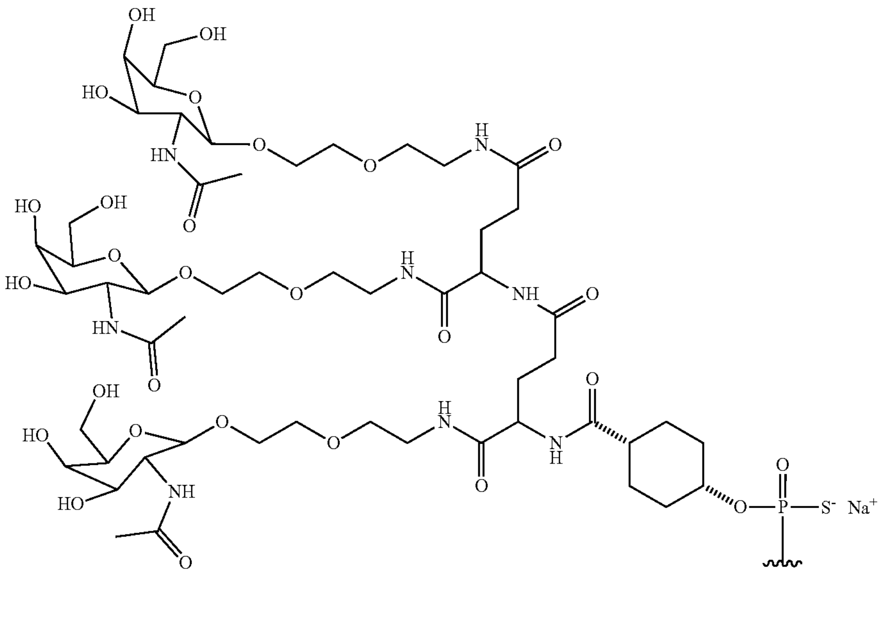

(shown in sodium salt form),

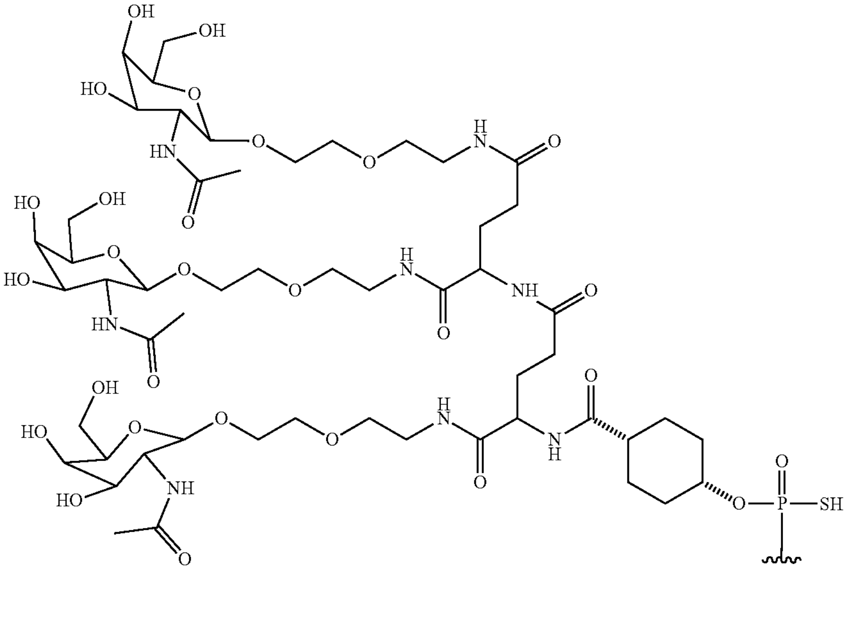

(shown in free acid form).

FIG. 4. Final Phase I study design and dose escalation schedule for the Phase I clinical study described in Example 2.

Figure 5:
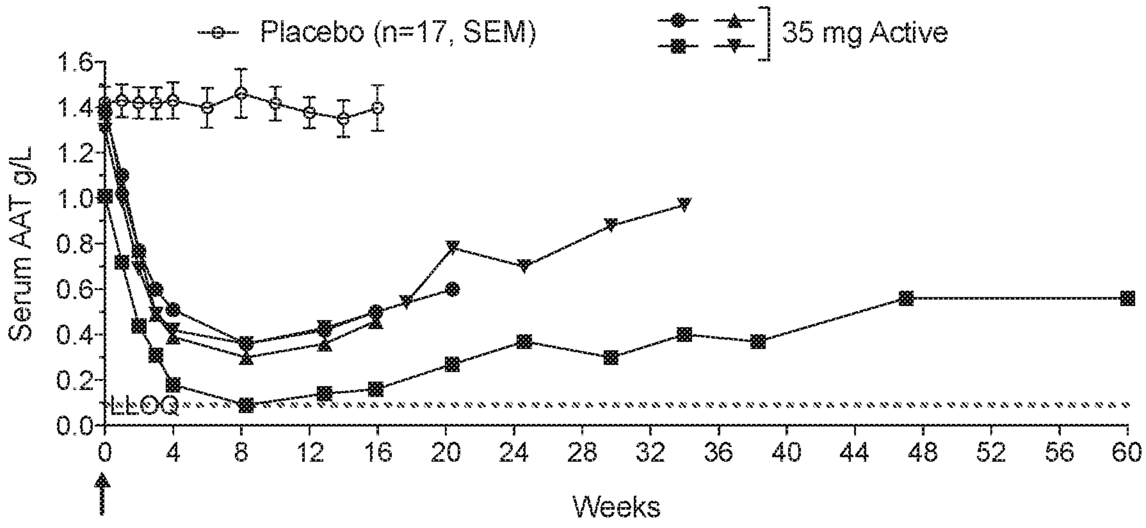

FIG. 5. Graph showing serum AAT levels in normal health human volunteers (NHV) administered with placebo (all Cohorts) or 35 mg of AAT RNAi Drug Substance (Cohort 1) from the Phase I clinical study described in Example 2. As shown in FIGS. 5 through 11. "Active" refers to the AAT RNAi Drug Substance described in Table 2 (administered as Formulated AAT RNAi Drug Substance as described in Table 3).

Figure 6:
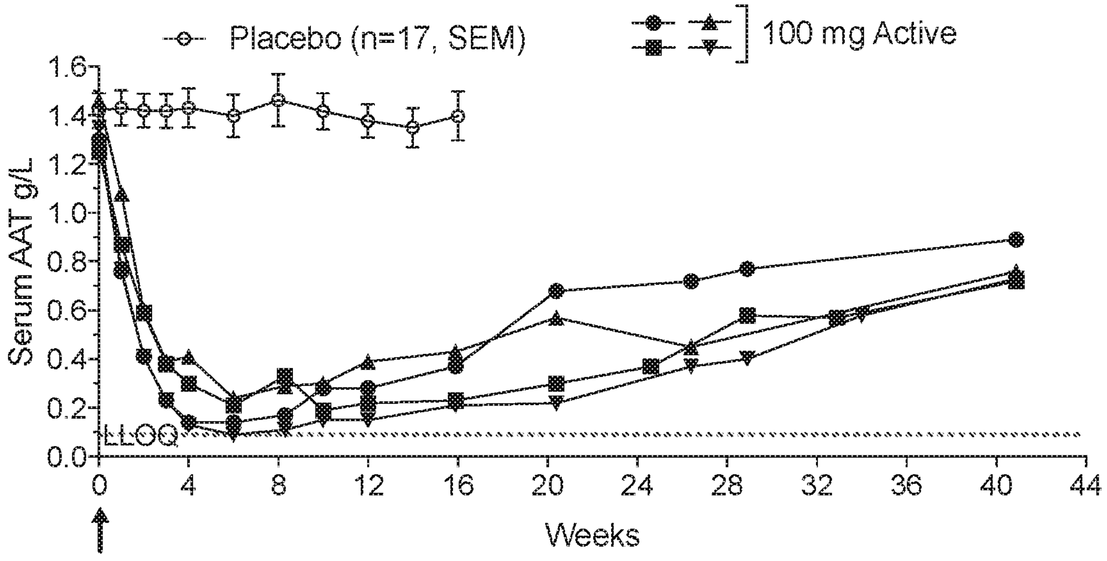

FIG. 6. Graph showing serum AAT levels in NHVs administered with placebo (all Cohorts) or a single 100 mg dose of AAT RNAi Drug Substance (Cohort 2b) from the Phase I clinical study described in Example 2.

Figure 7:
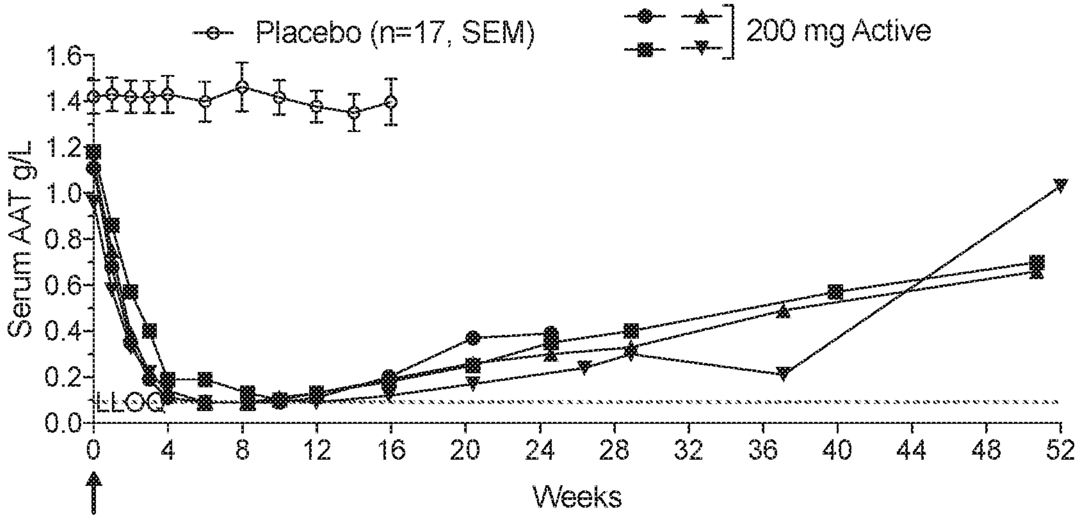

FIG. 7. Graph showing serum AAT levels in NHVs administered with placebo (all Cohorts) or a single 200 mg dose of AAT RNAi Drug Substance (Cohort 3b) from the Phase I clinical study described in Example 2.

Figure 8:
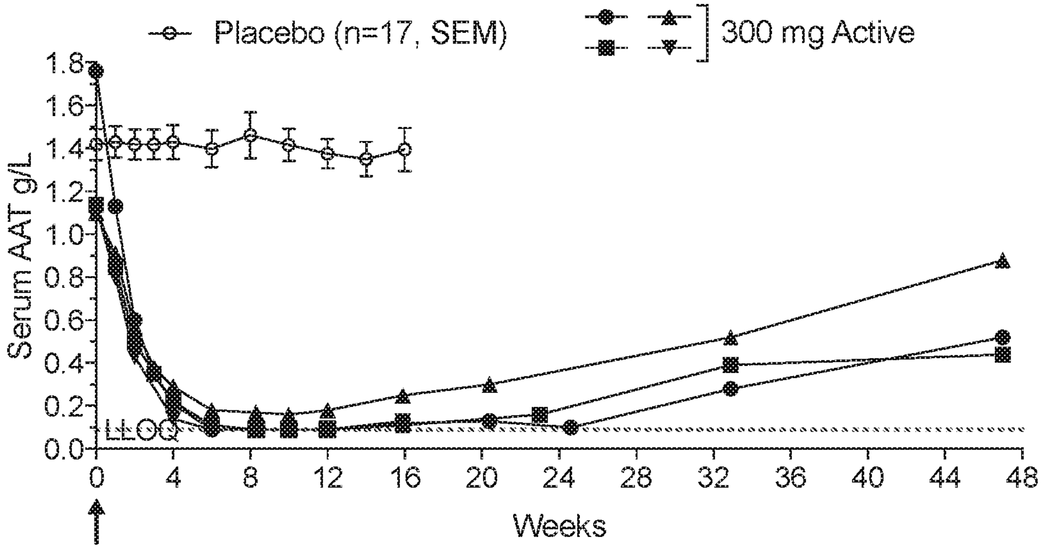

FIG. 8. Graph showing serum AAT levels in NHVs administered with placebo (all Cohorts) or a single 300 mg dose of AAT RNAi Drug Substance (Cohort 4b) from the Phase 1 clinical study described in Example 2.

Figure 9:
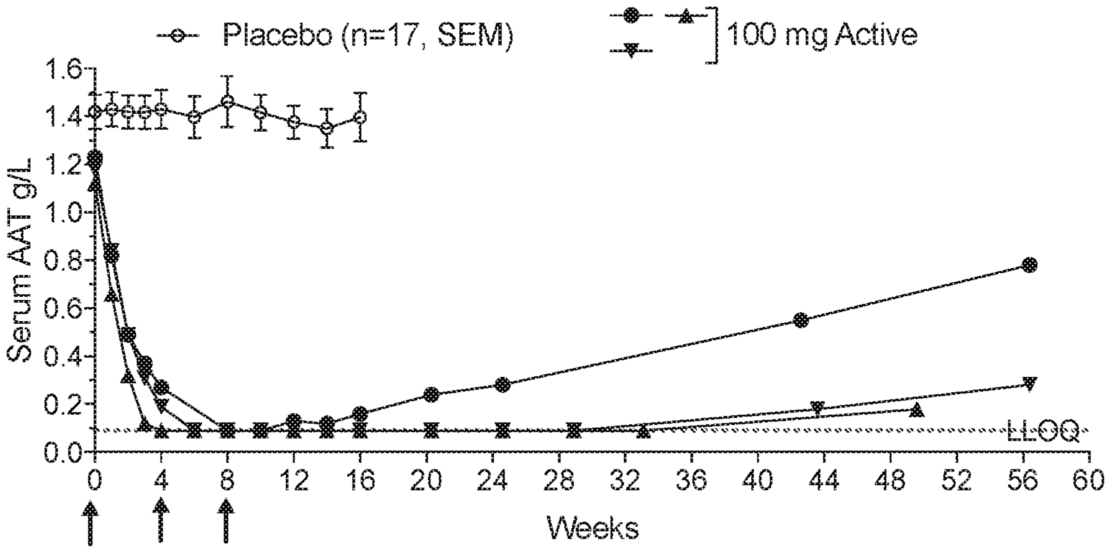

FIG. 9. Graph showing serum AAT levels in NHVs administered with placebo (all Cohorts) or three 100 mg doses of AAT RNAi Drug Substance administered monthly (Cohort 2) from the Phase I clinical study described in Example 2.

Figure 10:
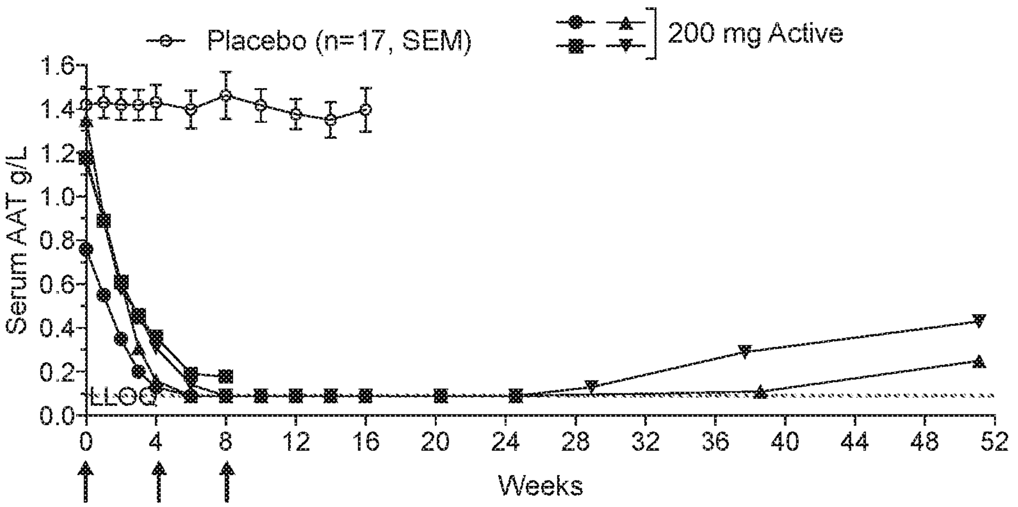

FIG. 10. Graph showing serum AAT levels in NHVs administered with placebo (all Cohorts) or three 200 mg doses of AAT RNAi Drug Substance administered monthly (Cohort 3) from the Phase I clinical study described in Example 2.

Figure 11:
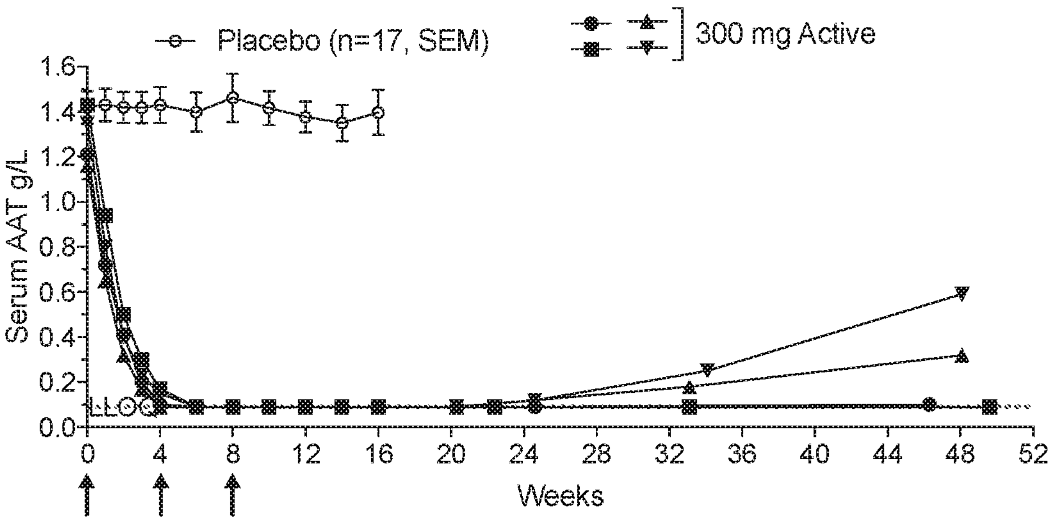

FIG. 11. Graph showing serum AAT levels in NHVs administered with placebo (all Cohorts) or three 300 mg doses of AAT RNAi Drug Substance administered monthly (Cohort 4) from the Phase I clinical study described in Example 2.

DETAILED DESCRIPTION

RNAi Agents

The methods described herein include the administration of a pharmaceutical composition to a human subject, wherein the pharmaceutical composition includes a composition that contains an RNA interference (RNAi) agent (referred to herein and in the art as an RNAi agent or an RNAi trigger) capable of inhibiting expression of an AAT gene. In some embodiments, the methods described herein include the administration of a pharmaceutical composition to a human subject, wherein the pharmaceutical composition includes the AAT RNAi Drug Substance described in Table 2 (also referred to as ADS-001). The compositions suitable for use in the methods disclosed herein are comprised of an RNAi agent that inhibits expression of an AAT gene in a human subject, and a targeting moiety or targeting group. In some embodiments, the RNAi agent includes the nucleotide sequences provided in Table 1A and 1B, and the sense strand of the RNAi agent is further linked or conjugated to a targeting group comprising three N-acetyl-galactosamine targeting moieties (see, e.g., Table B). An RNAi agent that inhibits expression of an AAT gene in a human subject is referred to as an "AAT RNAi agent."

In general, AAT RNAi agents comprise a sense strand (also referred to as a passenger strand) and an antisense strand (also referred to as a guide strand) that are annealed to form a duplex. The AAT RNAi agents disclosed herein include an RNA or RNA-like (e.g., chemically modified RNA) oligonucleotide molecule capable of degrading or inhibiting translation of messenger RNA (mRNA) transcripts of AAT mRNA in a sequence specific manner. The AAT RNAi agents disclosed herein may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that the AAT RNAi agents, as that term is used herein, operate primarily through the RNA interference mechanism, the disclosed RNAi agents are not bound by or limited to any particular pathway or mechanism of action. RNAi agents in general are comprised of a sense strand and an antisense strand that are each 16 to 49 nucleotides in length, and include, but are not limited to: short or small interfering RNAs (siRNAs), double-strand RNAs (dsRNA), micro RNAs (miRNAs), short hairpin RNAs (shRNA), and dicer substrates.

The length of an AAT RNAi agent sense strand is typically 16 to 49 nucleotides in length, and the length of an AAT RNAi agent antisense strand is typically 18 to 49 nucleotides in length. In some embodiments, the sense and antisense strands are independently 17 to 26 nucleotides in length. In some embodiments, the sense and antisense strands are independently 21 to 26 nucleotides in length. In some embodiments, the sense and antisense strands are independently 21 to 24 nucleotides in length. In some embodiments, the sense and/or antisense strands are independently 16, 17, 18, 19, 20, 21, 22, 23, 24, 25, 26, 27, 28, 29, or 30 nucleotides in length. In some embodiments, the sense strand and the antisense strand are both 21 nucleotides in length. The sense and antisense strands can be either the same length or different lengths. The sense and antisense strands can also form overhanging nucleotides on one or both ends of the AAT RNAi agent.

AAT RNAi agents inhibit, silence, or knockdown AAT gene expression. As used herein, the terms "silence," "reduce," "inhibit," "down-regulate," or "knockdown," when referring to expression of AAT, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agent as compared to a second cell, group of cells, tissue, organ, or subject that has not or have not been so treated. In some instances, the reduction in gene expression is measured by comparing the baseline levels of AAT mRNA or AAT protein in a human subject prior to administration of a composition that comprises an AAT RNAi agent, with the AAT mRNA or AAT protein levels after administration of the therapeutic.

AAT gene inhibition, silencing, or knockdown may be measured by any appropriate assay or method known in the art. The non-limiting Examples set forth herein, as well as the examples set forth in International Patent Application Publication No. WO 2018/132432 (Patent Application No. PCT/US2018/013102), which is incorporated by reference herein in its entirety, provide certain examples of appropriate assays for measuring AAT gene expression inhibition. A reference AAT mRNA gene transcript (SERPINA1) for normal humans (referred to as transcript variant 1; GenBank NM_000295.4) can be found at SEQ ID NO:1.

AAT RNAi agents suitable for use in the methods disclosed herein can be covalently linked or conjugated to a targeting group that includes one or more N-acetyl-galactosamine moieties. In embodiments, AAT RNAi agents suitable for use in the methods disclosed herein are covalently linked or conjugated to a targeting group that includes one or more N-acetyl-galactosamine moieties thereby forming the AAT RNAi Drug Substance described in Table 2. In some embodiments, the methods described herein include the administration of the AAT RNAi Drug Substance described in Table 2. The AAT RNAi Drug Substance described in Table 2 includes the AAT RNAi agent shown in Table 1A (antisense strand) and Table 1B (sense strand). The N-acetyl-galactosamine moieties facilitate the targeting of the AAT RNAi agent to the asialoglycoprotein receptors (ASGPr) readily present on the surface of hepatocytes, which leads to internalization of the AAT RNAi agent by endocytosis or other means.

The AAT RNAi agents that can be suitable for use in the methods disclosed herein include an antisense strand that has a region of complementarity to at least a portion of an AAT mRNA. AAT RNAi agents and AAT RNAi Drug Substances suitable for use in the disclosed methods are described in International Patent Application Publication No. WO 2018/132432 (Patent Application No. PCT/US2018/013102), which as previously noted is incorporated by reference herein in its entirety.

As used herein, the terms “sequence” and “nucleotide sequence” mean a succession or order of nucleobases or nucleotides, described with a succession of letters using standard nomenclature. As used herein, the terms “nucleobase” and “nucleotide” have the same meaning as commonly understood in the art.

As used herein, the term “complementary,” when used to describe a first nucleotide sequence (e.g., RNAi agent antisense strand) in relation to a second nucleotide sequence (e.g., RNAi agent sense strand or targeted mRNA sequence), means the ability of an oligonucleotide that includes the first nucleotide sequence to hybridize (form base pair hydrogen bonds under mammalian physiological conditions (or otherwise suitable conditions) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, “perfectly complementary” or “fully complementary” means that all (100%) of the bases in a contiguous sequence of a first oligonucleotide will hybridize with the same number of nucleotides in a contiguous sequence of a second oligonucleotide. The contiguous sequence may comprise all or a part of a first or second nucleotide sequence.

As used herein, “partially complementary” means that in a hybridized pair of nucleotide sequences, at least 70%, but not all, of the bases in a contiguous sequence of a first oligonucleotide will hybridize with the same number of bases in a contiguous sequence of a second polynucleotide.

As used herein, “substantially complementary” means that in a hybridized pair of nucleotide sequences, at least 85%, but not all, of the bases in a contiguous sequence of a first oligonucleotide will hybridize with the same number of bases in a contiguous sequence of a second polynucleotide. The terms “complementary,” “fully complementary,” “partially complementary.” and “substantially complementary” herein are used with respect to the nucleotide matching between the sense strand and the antisense strand of an RNAi agent, or between the antisense strand of an RNAi agent and a sequence of an AAT mRNA.

As used herein, the term “substantially identical” or “substantially identity” as applied to nucleic acid sequence means that a nucleic acid sequence comprises a sequence that has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

Modified Nucleotides and Modified Internucleoside Linkages

The AAT RNAi agents disclosed herein can be comprised of modified nucleotides, which can preserve activity of the RNAi agent while at the same time increasing the serum stability, as well as minimize the possibility of activating interferon activity in humans. As used herein, a “modified nucleotide” is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include any known modified nucleotides known in the art, including but not limited to, deoxyribonucleotides, nucleotide mimics, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-arabino nucleotides, 5'-Me, 2'-fluoro nucleotides, morpholino nucleotides, vinyl phosphonate-containing nucleotides, and cyclopropyl phosphonate-containing nucleotides. In some embodiments, the modified nucleotides of an AAT RNAi agent are 2'-modified nucleotides (i.e. a nucleotide with a group other than a hydroxyl group at the 2' position of the five-membered sugar ring), 2'-modified nucleotides include, but are not limited to, 2'-O-methyl nucleotides, 2'-deoxy-2'-fluoro nucleotides (commonly referred to simply as 2'-Fluoro nucleotides), 2'-deoxy nucleotides, 2'-methoxyethyl (2'-O-2-methoxyethyl) nucleotides, 2'-amino nucleotides, and 2'-alkyl nucleotides. Additional 2'-modified nucleotides are known in the art. It is not necessary for all nucleotides in a given RNAi agent to be uniformly modified. Additionally, more than one modification can be incorporated in a single AAT RNAi agent or even in a single nucleotide thereof. The AAT RNAi agent sense strands and antisense strands can be synthesized and/or modified by methods known in the art. Modification at one nucleotide is independent of modification at another nucleotide.

In some embodiments, the nucleobase (often referred to as simply the “base”) may be modified. As is commonly used in the art, natural nucleobases include the primary purine bases adenine and guanine, and the primary pyrimidine bases cytosine, thymine, and uracil. A nucleobase may be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

Modified nucleobases include, for example, 5-substituted pyrimidines, 6-azapyrimidines and N-2, N-6 and O-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an AAT RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being ribonucleotides. As used herein, an antisense sense strand wherein substantially all of the nucleotides present are modified nucleotides is an antisense strand having two or fewer (i.e., 0, 1, or 2) nucleotides in the sense strand being ribonucleotides.

In some embodiments, one or more nucleotides of an AAT RNAi agent are linked by non-standard linkages or backbones (i.e., modified internucleoside linkages or modified backbones). Modified internucleoside linkages or backbones include, but are not limited to, phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an AAT RNAi agent can contain 1, 2, 3, 4, 5, or 6 phosphorothioate linkages, an antisense strand of an AAT RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an AAT RNAi agent can contain 1, 2, 3, or 4 phosphorothioate linkages, an antisense strand of an AAT RNAi agent can contain 1, 2, 3, or 4 phosphorothioate linkages, or both the sense strand and the antisense strand independently can contain 1, 2, 3, or 4 phosphorothioate linkages.

In some embodiments, an AAT RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, phosphorothioate internucleoside linkages are used to link the terminal nucleotides in the sense strand to capping residues present at the 5-end, the 3'-end, or both the 5'- and 3'-ends of the nucleotide sequence. In some embodiments, phosphorothioate internucleoside linkages are used to link a targeting group to the sense strand.

In some embodiments, an AAT RNAi agent antisense strand contains three or four phosphorothioate internucleoside linkages. In some embodiments, an AAT RNAi agent antisense strand contains three phosphorothioate internucleoside linkages. In some embodiments, the three phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, an AAT RNAi agent contains at least two phosphorothioate internucleoside linkages in the sense strand and three or four phosphorothioate internucleoside linkages in the antisense strand.

In some embodiments, an AAT RNAi agent contains one or more modified nucleotides and one or more modified internucleoside linkages. In some embodiments, a 2'-modified nucleoside is combined with modified internucleoside linkage.

Capping Residues or Moieties

In some embodiments, the sense strand may include one or more capping residues or moieties, sometimes referred to in the art as a "cap." a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table A). (See, e.g., F. Czaudema, Nucleic Acids Res., 2003, 31(11), 2705-16). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside link-ages. The chemical structures for inverted abasic deoxyribose residues are shown in Table A below, as well as in the chemical structures shown in FIGS. 1A to 1E and FIGS. 2A to 2E.

TABLE A

| Inverted Abasic (Deoxyribose) Chemical Structures |
|---|
| When positioned internally on oligonucleotide: |
| linkage towards 5′ end of oligonucleotide 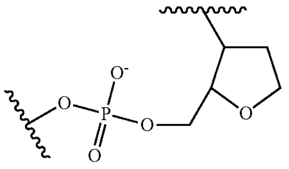 linkage towards 3′ end of oligonucleotide |
| (invAb) |
| When positioned internally on oligonucleotide: |
| linkage towards 5′ end of oligonucleotide 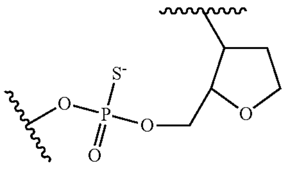 linkage towards 3′ end of oligonucleotide |
| (invAb)s |
| When positioned at the 3' terminal end of oligonucleotide: |
| linkage towards 5′ end of oligonucleotide 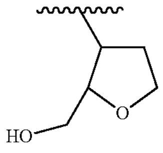 |
| (invAb) |

Targeting Moieties and Groups

An AAT RNAi agent can be conjugated to one or more non-nucleotide groups including, but not limited to, a targeting moiety or a targeting group. A targeting moiety or targeting group can enhance targeting or delivery of the RNAi agent. Examples of targeting moieties and targeting groups are known in the art. Specific examples of the (NAG37)s targeting group used in the AAT RNAi Drug Substance described in Table 2 herein, which includes three N-acetyl-galactosamine targeting moieties, is provided in Table B. The targeting moiety or targeting group can be covalently linked to the 3' and/or 5' end of either the sense strand and/or the antisense strand. In some embodiments, an AAT RNAi agent contains a targeting group linked to the 3' and/or 5' end of the sense strand. In some embodiments, a targeting group is linked to the 5' end of an AAT RNAi agent sense strand. In some embodiments, the targeting group comprises, consists essential of, or consists of the structure (NAG37)s, and is linked to the 5' end of an AAT RNAi agent sense strand. A targeting group can be linked directly or indirectly to the RNAi agent via a linker/linking group. In some embodiments, a targeting group is linked to the RNAi agent via a labile, cleavable, or reversible bond or linker. In some embodiments, a targeting group is linked to an inverted abasic residue at the 5' end of the sense strand.

Targeting groups or targeting moieties can enhance the pharmacokinetic or biodistribution properties of a conjugate or RNAi agent to which they are attached to improve cell-specific distribution and cell-specific uptake of the conjugate or RNAi agent. In some embodiments, a targeting group enhances endocytosis of the RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules.

In some embodiments, a targeting group comprises an asialoglycoprotein receptor ligand. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formyl galactosamine, N-acetyl-galactosamine, N-propionyl-galactosamine, N-n-butanoyl-galactosamine, and N-iso-butanoyl-galactosamine (see for example: S. T. Iobst and K. Drickamer, J. B. C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative) or multimeric (e.g., having multiple galactose derivatives). The galactose derivative or galactose derivative "cluster" can be attached to the 3' or 5' end of the sense or antisense strand of the RNAi agent using methods known in the art.

In some embodiments, a targeting group comprises a galactose derivative cluster. As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosomines. In some embodiments, the galactose derivative cluster comprises three N-acetyl-galactosomines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosomines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem. 1995 Vol. 39 p. 1538-1546). The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

The preparation of targeting groups, such as galactose derivative clusters that include N-acetyl-galactosamine, is described in, for example. International Patent Application Publication No. WO 2018/044350 (Patent Application No. PCT/US2017/021147) and International Patent Application Publication No. WO 2017/156012 (Patent Application No. PCT/US2017/021175), the contents of both of which are incorporated by reference herein in their entirety.

For example, the targeting ligand conjugated to the AAT RNAi agent described in Tables 1A and 1B has the chemical structure of (NAG37)s, as shown in the following Table B.

TABLE B

| Chemical Structure of (NAG-37)s. |
|---|
| 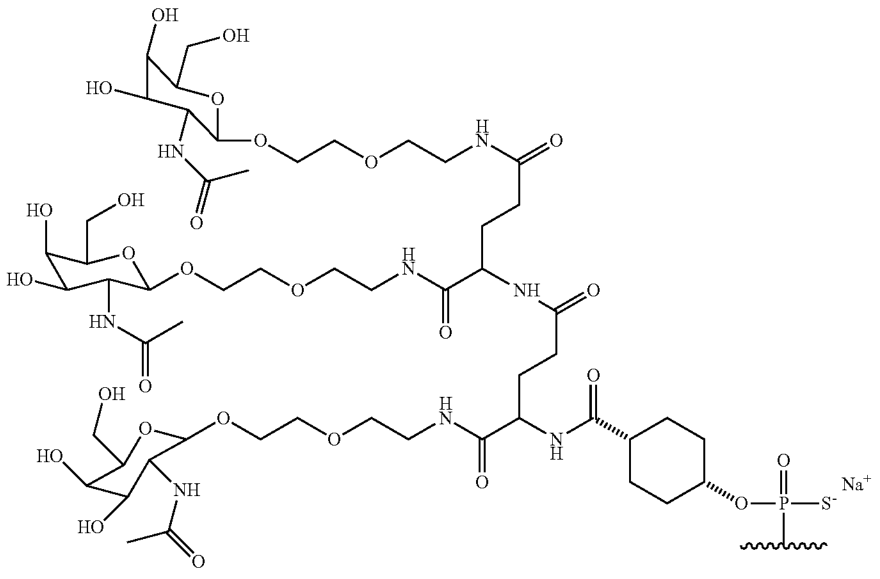 |
| ((NAG37)s shown in sodium salt form) |

TABLE B-continued

| Chemical Structure of (NAG-37)s. |
|---|
| 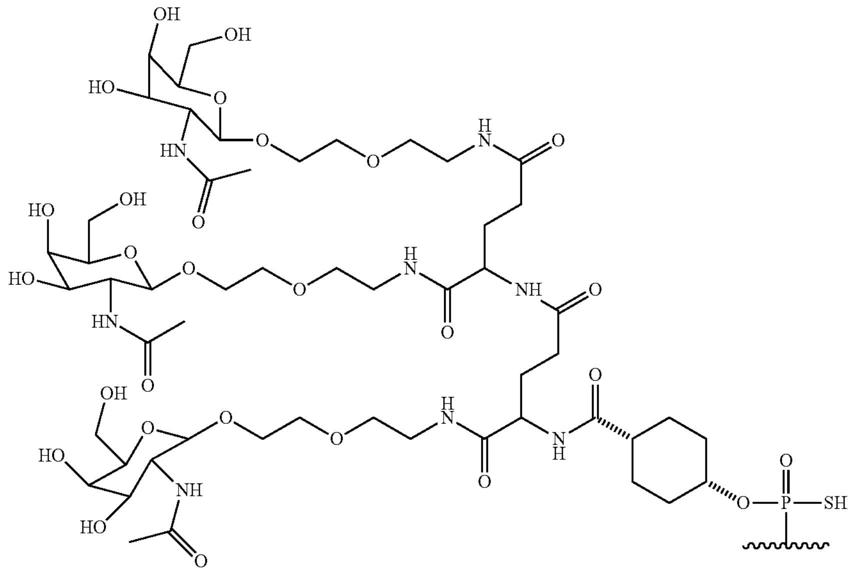 |
| ((NAG37)s shown in free acid form) |

AAT RNAi Agents and AAT RNAi Drug Substance (ADS-001)

In some embodiments, the AAT RNAi agent used in the methods disclosed herein have the nucleotide sequences of the AAT RNAi Drug Substance (ADS-001) shown in Table 2. The nucleotide sequences of the AAT RNAi agent found in AAT RNAi Drug Substance include an antisense strand nucleotide sequence as set forth in the following Table 1A, and a sense strand nucleotide sequence as set forth in the following Table 1B.

TABLE 1A

AAT RNAi Agent Antisense Strand Sequence

| SEQ ID NO. | Antisense Sequence (Modified) (5' → 3') | SEQ ID NO. | Underlying Base Sequence (5' → 3') |
|---|---|---|---|
| 2 | usGfsuUfaAfacaugCfcU faAfaCfgCfsu | 3 | UGUUAAACAUGCCUAAAC GCU |

TABLE 1B

AAT RNAi Agent Sense Strand Nucleotide Sequence (shown modified version without inverted abasic residues or NAG targeting group present in AAT RNAi Drug Substance)

| SEQ ID NO. | Antisense Sequence (Modified) (5' → 3') | SEQ ID NO. | Underlying Base Sequence (5' →3') |
|---|---|---|---|
| 4 | agcguuuaGfGfCfauguuu aaca | 5 | AGCGUUUAGGCAUGUUU AACA |

As used in Tables 1A, 1B, and 2 herein, the following notations are used to indicate modified nucleotides, targeting groups, and linking groups: A, G, C, and U represent adenosine, cytidine, guanosine, or undine; a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage; (invAb) represents an inverted abasic deoxyribose residue (see Table A); and (NAG37)s represents the structure shown in Table B, above.

As the person of ordinary skill in the art would readily understand, unless otherwise indicated by the sequence (such as, for example, by a phosphorothioate linkage "s"), when present in a strand, the monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand. Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the AAT RNAi agents and compositions that include AAT RNAi agents disclosed herein.

Each sense strand and/or antisense strand can have any targeting groups or linking groups listed above, as well as other targeting or linking groups, conjugated to the 5' and/or 3' end of the sequence.

The AAT RNAi agent antisense strand sequence is designed to target mRNA transcripts from both normal and mutant AAT genes, thereby silencing translation of mutant Z-AAT proteins using an RNA interference mechanism for human subjects with AATD.

In some embodiments, the methods disclosed herein use the AAT RNAi Drug Substance set forth in the following Table 2:

TABLE 2

| AAT RNAi Drug Substance (ADS-001) | | |
|---|---|---|
| Sense and Antisense Strands (The sense and antisense strands are annealed to form a duplex): | | |
| Sense Strand (Modified Sequence) (5' → 3'): | (NAG37)s(invAb)sagcguuuaGfGfCfauguuuaacas (invAb) | (SEQ ID NO: 6) |
| Antisense Strand (Modified Sequence) (5' → 3'): | usGfsuUfaAfacaugCfcUfaAfaCfgCfsu | (SEQ ID NO: 2) |
| Chemical Formula: | $C_{493}H_{610}F_{11}N_{163}N_{a43}O_{312}P_{43}S_6$ ($N_{a+}$ form)<br>$C_{493}H_{653}F_{11}N_{163}O_{312}P_{43}S_6$ ($H_+$ form) | |
| Molecular Weight: | 16532.9 Da ($N_{a+}$ form)<br>15587.6 Da ($H_+$ form) | |
| Physical Appearance: | White to Off-white Powder | |

Figure 1A:
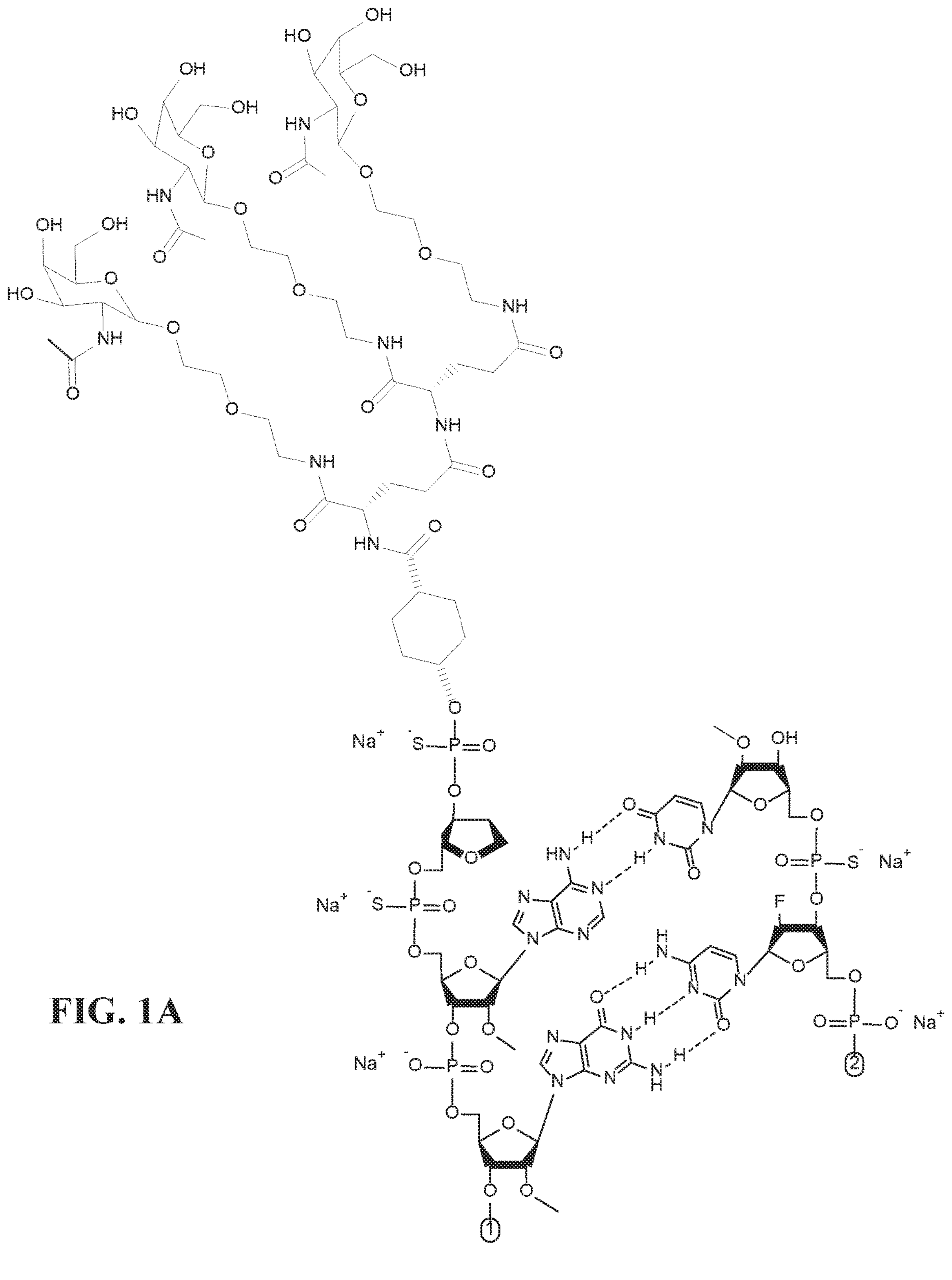
FIG. 1A to 1E. Chemical structure representation of AAT RNAi Drug Substance described in Table 2 (referred to herein as ADS-001; i.e., AAT RNAi agent conjugated to a tridentate N-acetyl-galactosamine targeting group at the 5' terminal end of the sense strand), shown in a sodium salt form.
Figure 1B:
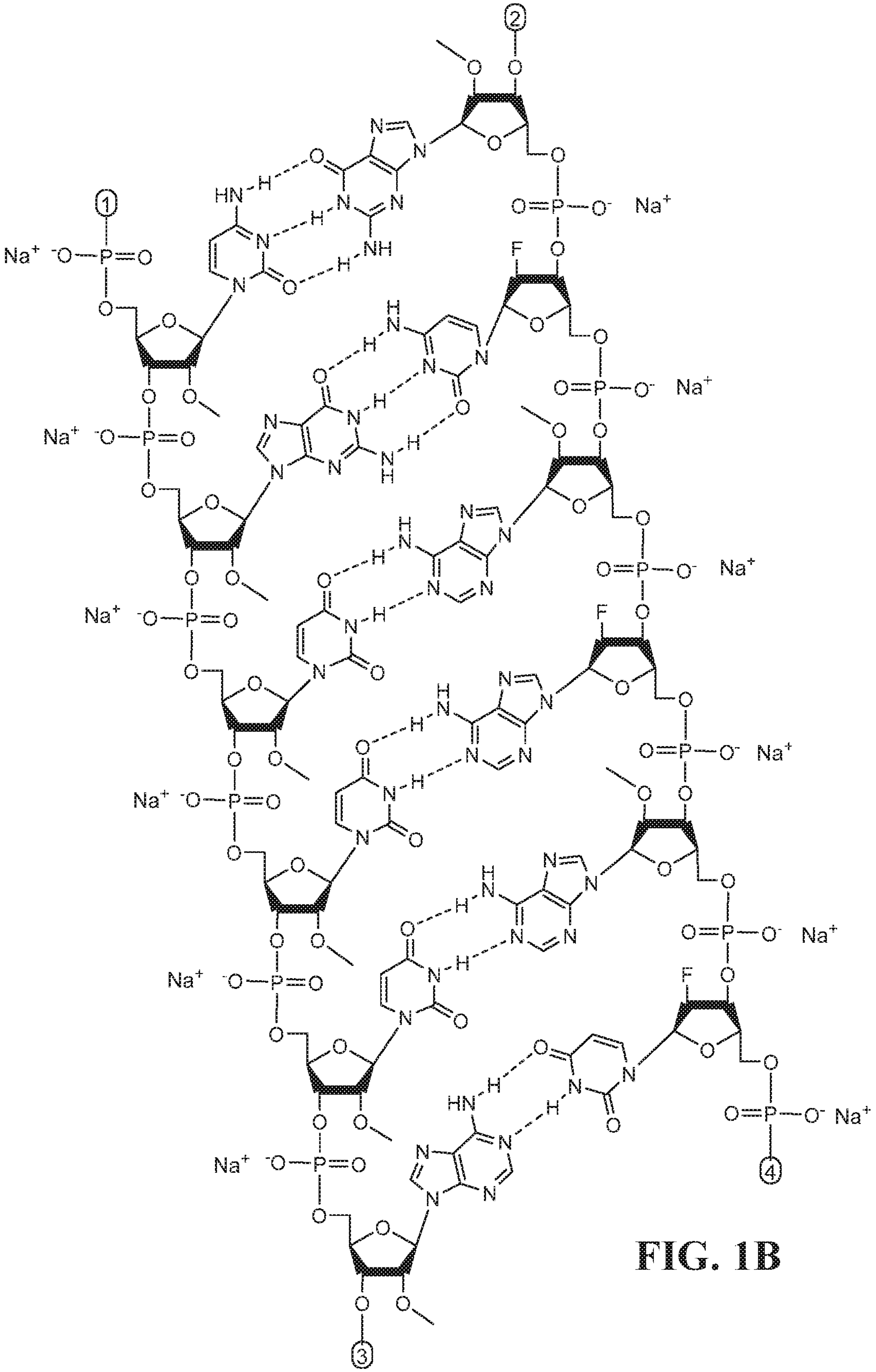
Figure 1C:
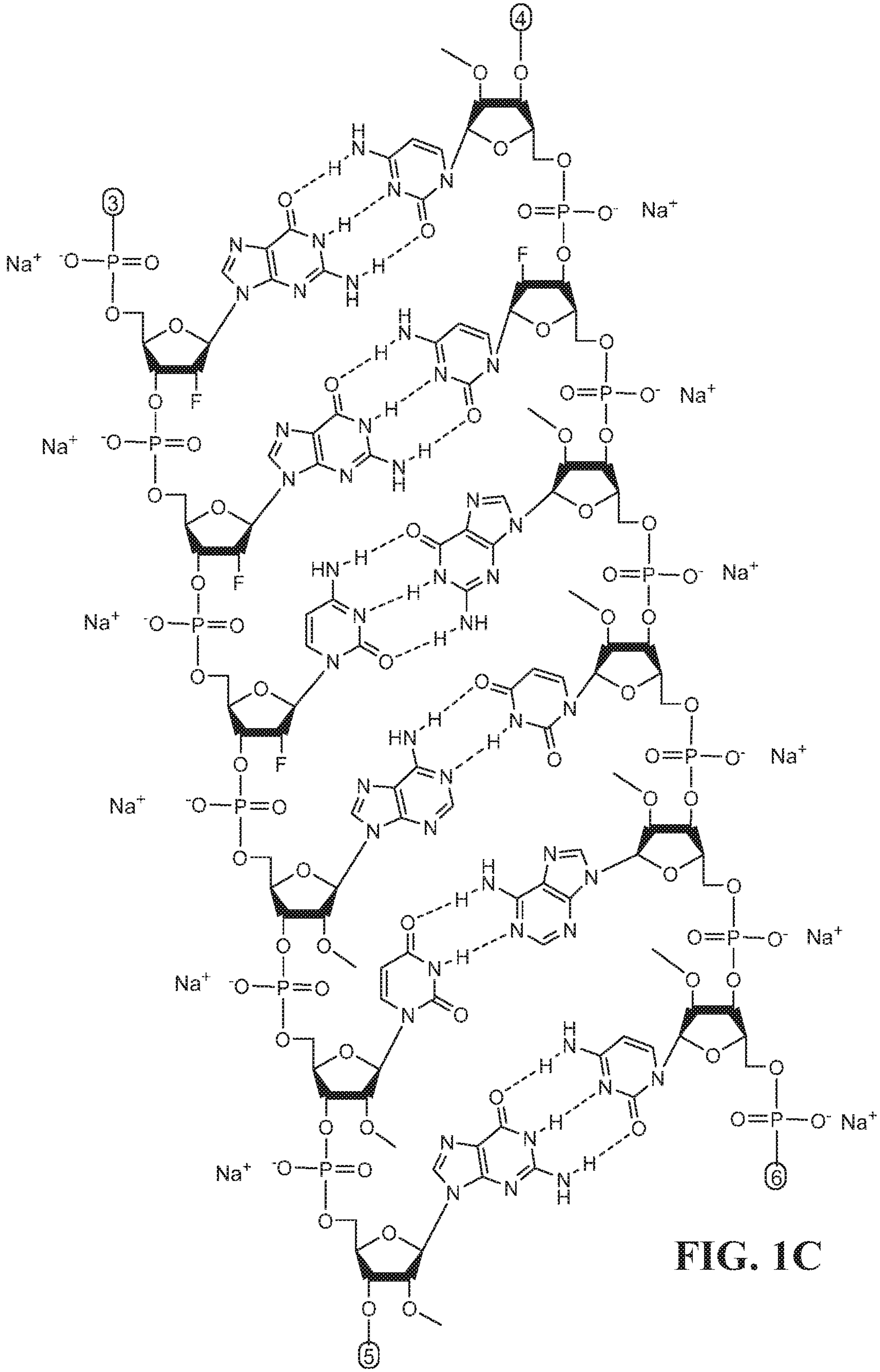
Figure 1D:
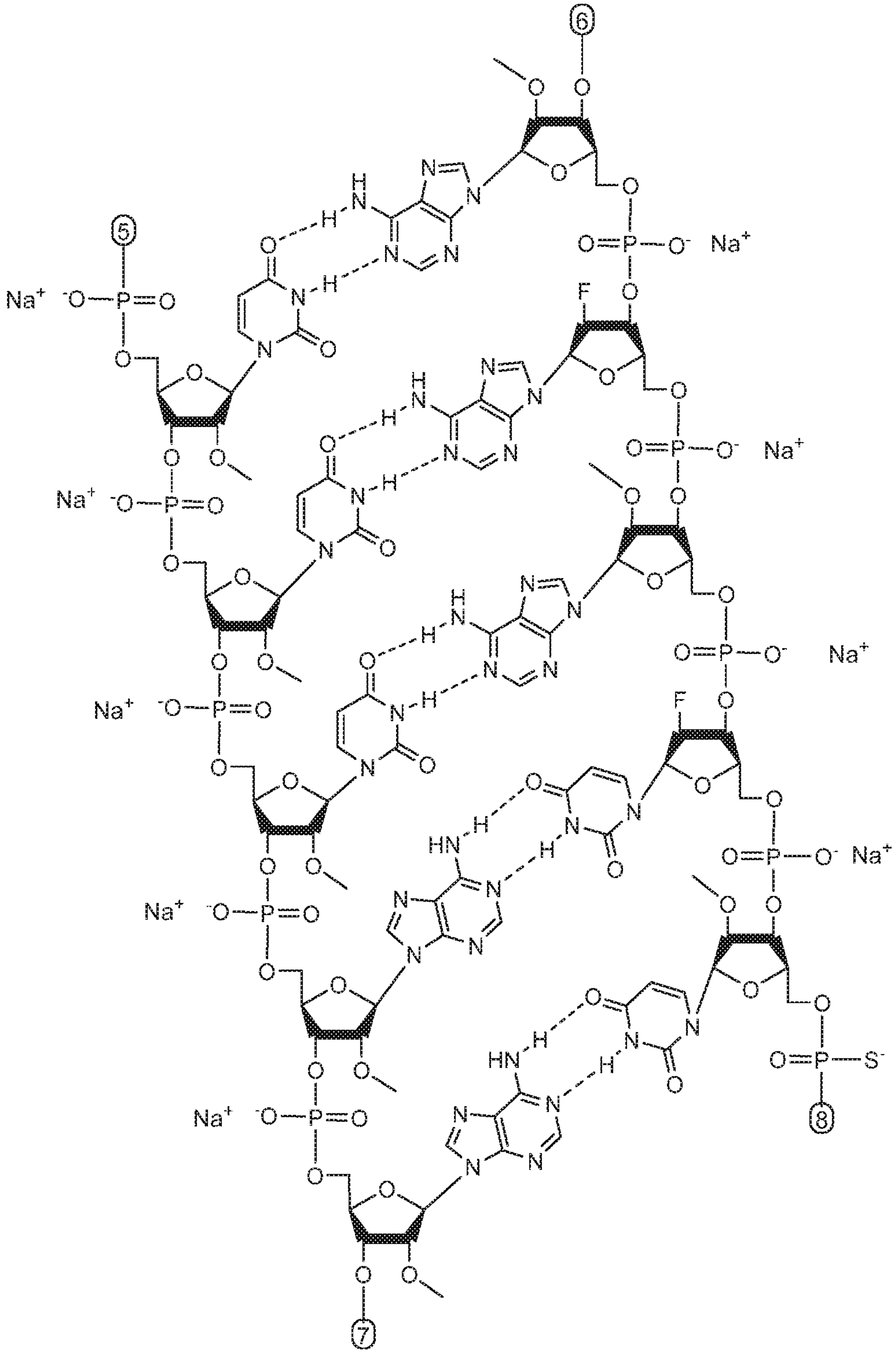
Figure 1E:
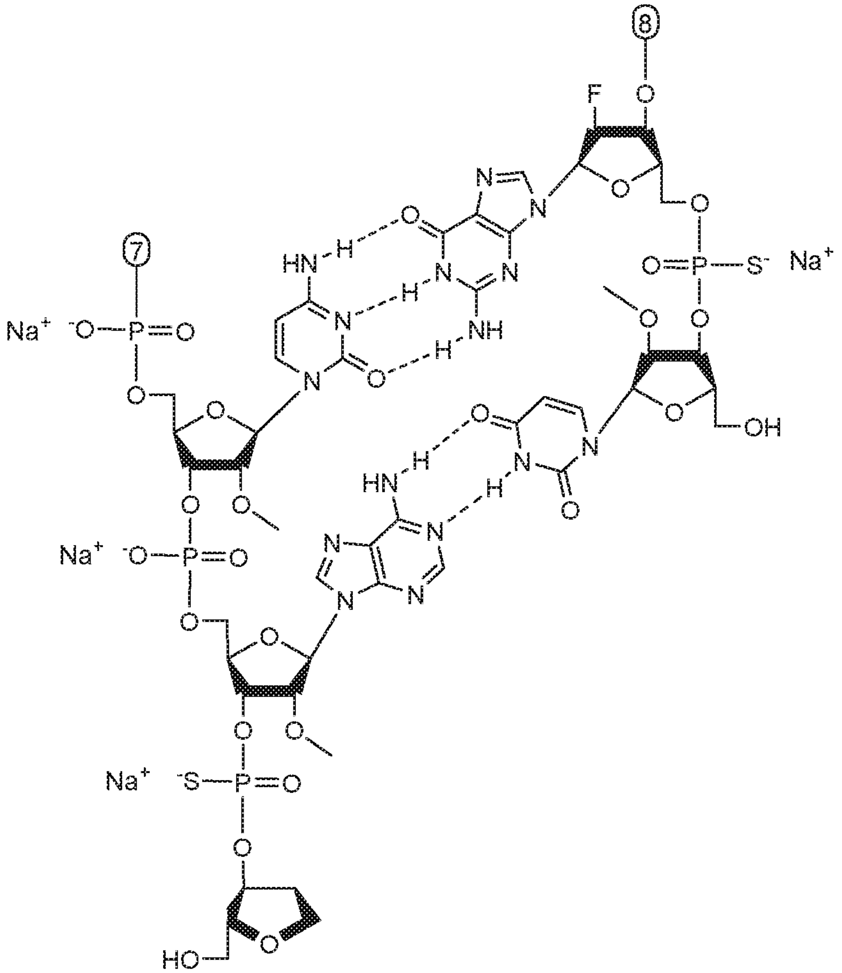
Figure 2A:
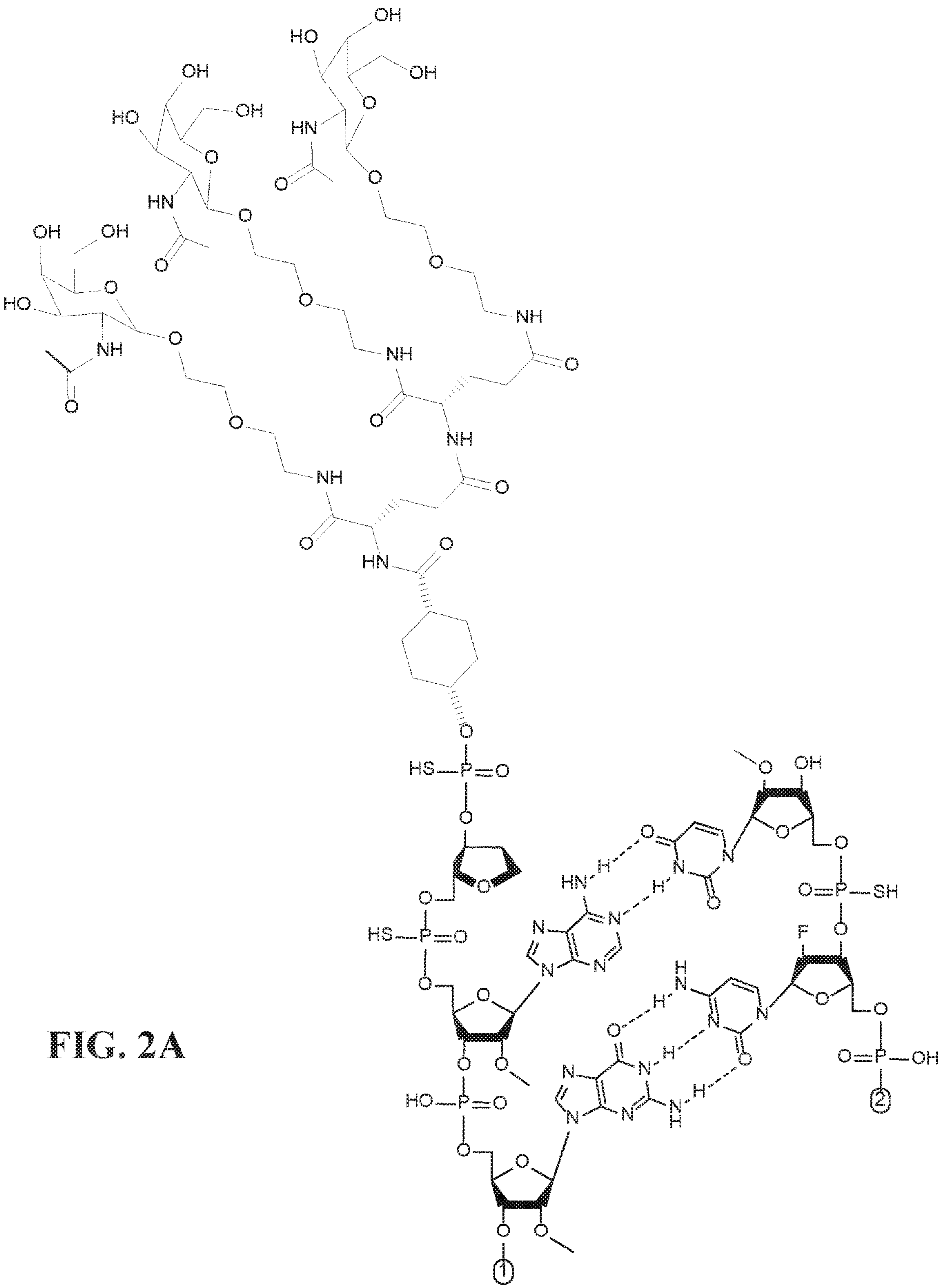
FIG. 2A to 2E. Chemical structure representation of AAT RNAi Drug Substance described in Table 2, shown in a free acid form.
Figure 2B:
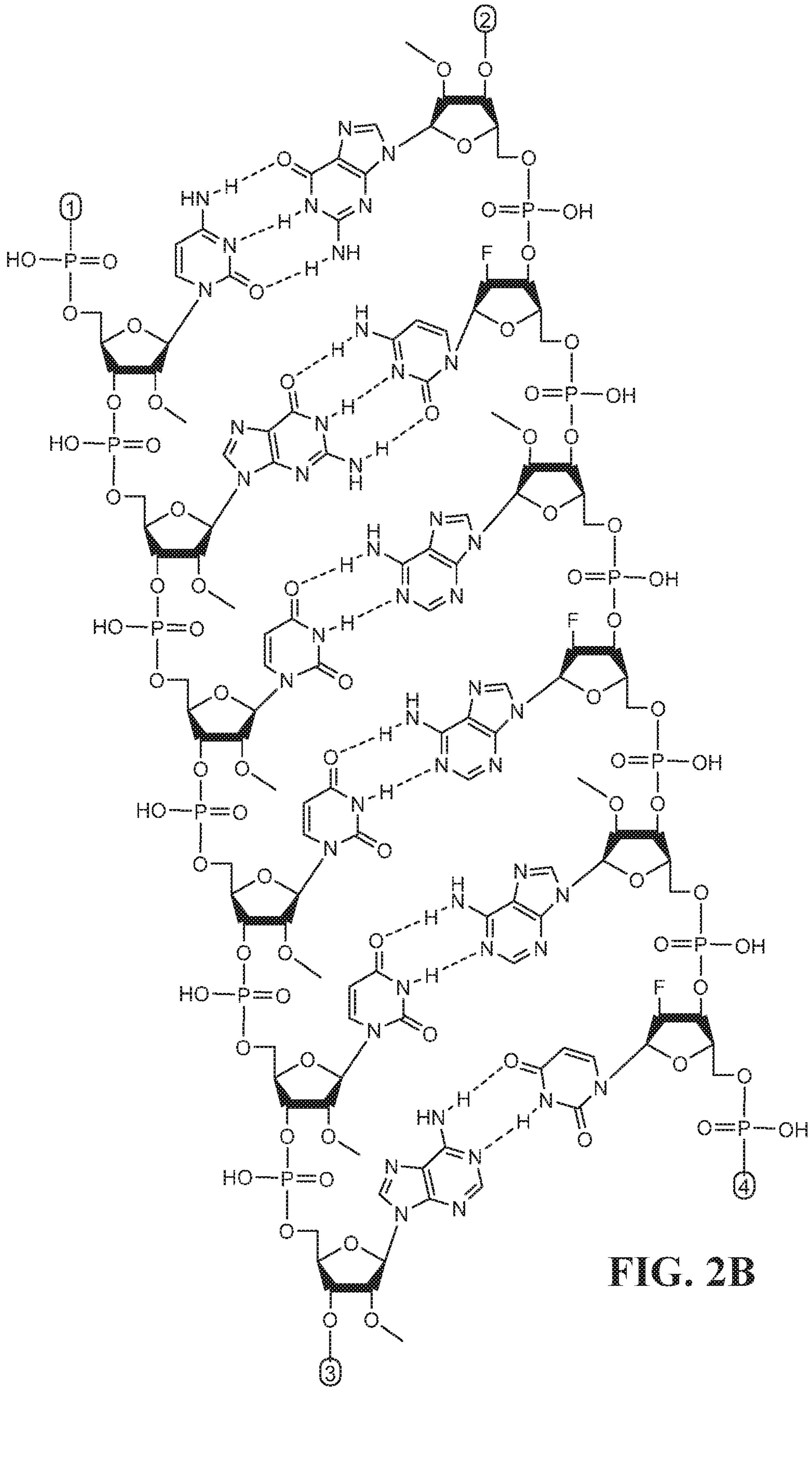
Figure 2C:
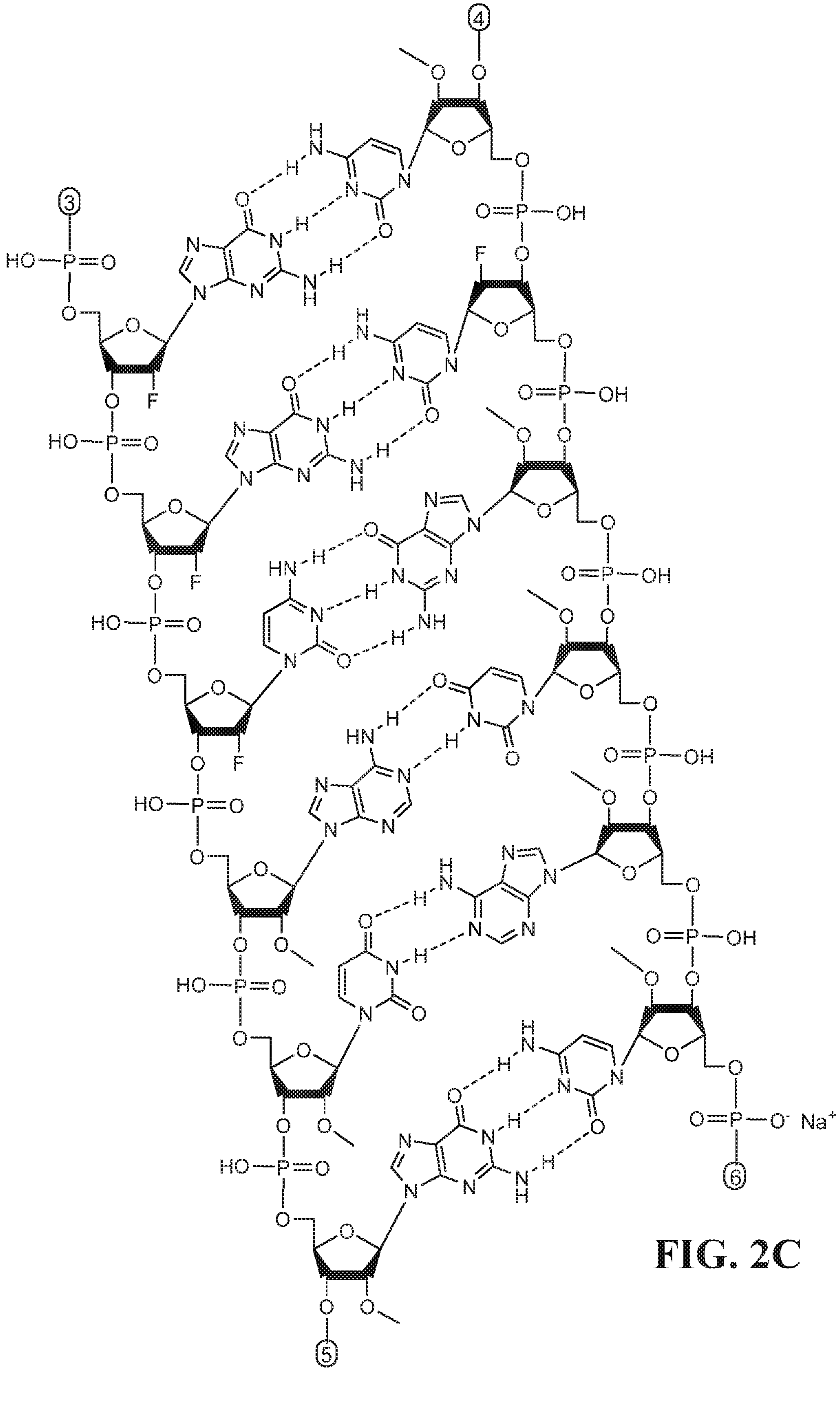
Figure 2D:
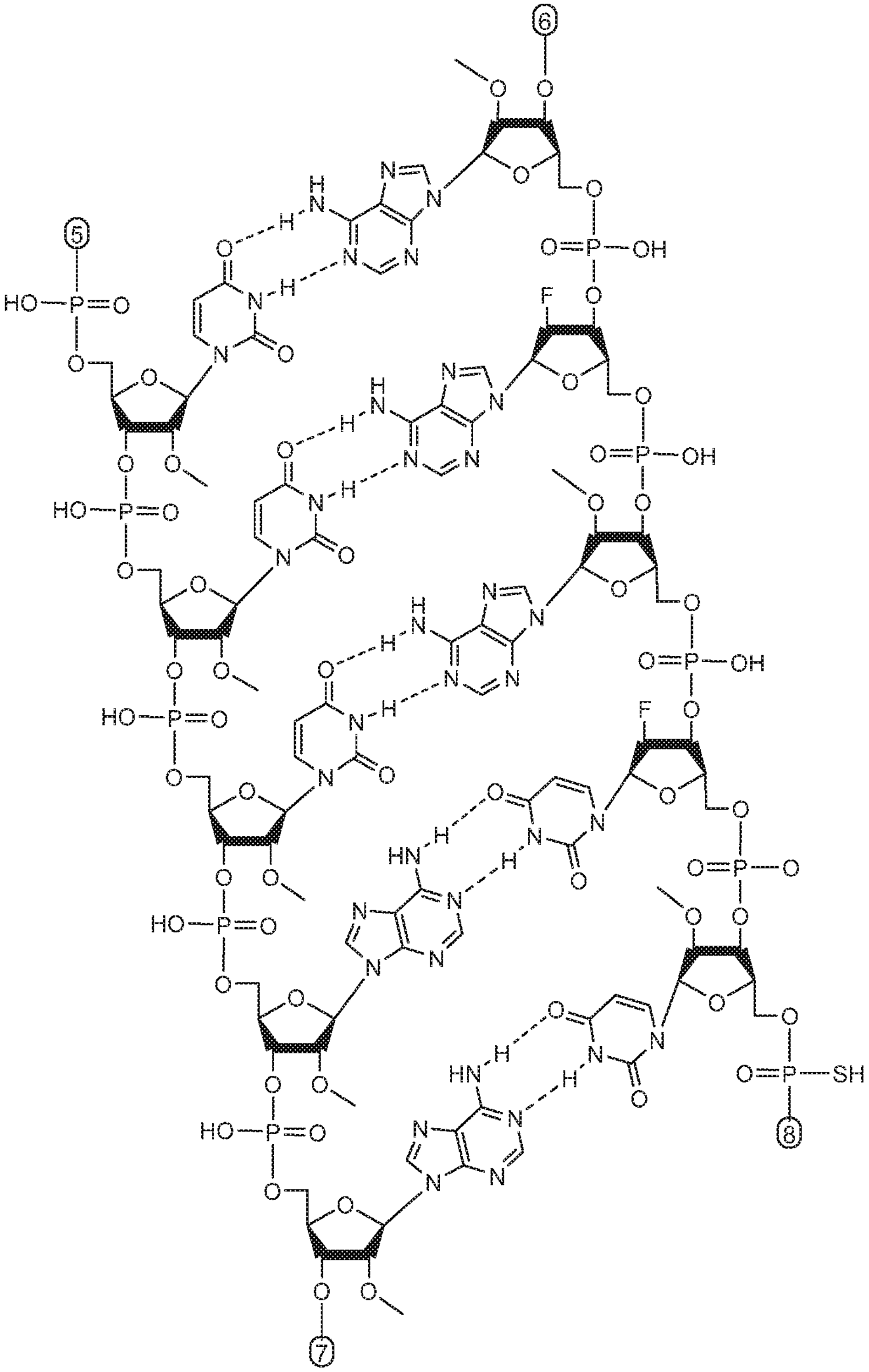
Figure 2E:
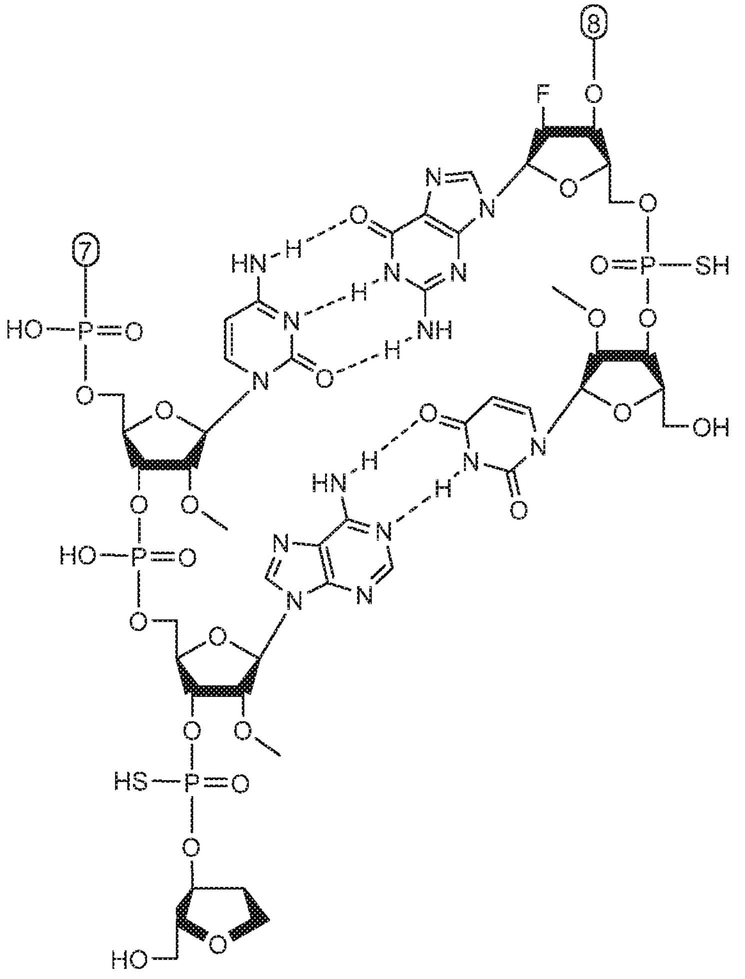
Figure 3:
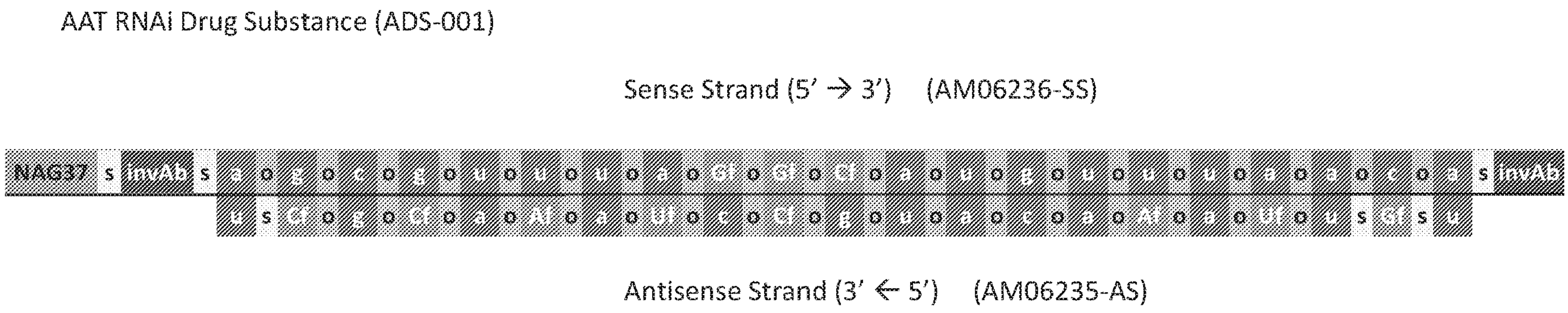
FIG. 3. Schematic diagram of the modified sense and antisense strands of AAT RNAi Drug Substance described in Table 2 (referred to herein as ADS-001; i.e., AAT RNAi agent conjugated to a tridentate N-acetyl-galactosamine targeting group at the 5' terminal end of the sense strand). The following abbreviations are used in FIG. 3: a, c, g, and u are 2'-O-methyl modified nucleotides; Af, Cf, Gf, and Uf are 2'-fluoro (also referred to in the art as 2'-deoxy-2'-fluoro) modified nucleotides: o is a phosphodiester linkage; s is a phosphorothioate linkage; invAb is an inverted abasic residue or subunit; and (NAG37)s is a tridentate N-acetyl-galactosamine targeting ligand having the following chemical structure.

A schematic representation of AAT RNAi Drug Substance (ADS-001) is shown in FIG. 3, and full chemical structure representations are shown in FIGS. 1A to 1E (sodium salt form) and FIGS. 2A to 2E (free acid form). In some embodiments, the AAT RNAi Drug Substance is prepared or provided as a salt, mixed salt, or a free-acid. In preferred embodiments, the form is a sodium salt.

Pharmaceutical Compositions and Formulations

The AAT RNAi agents suitable for use in the methods disclosed herein can be prepared as pharmaceutical compositions or formulations for administration to human subjects. The pharmaceutical compositions can be used to treat a subject having a disease or disorder that would benefit from inhibition of expression of AAT mRNA or reduction in the level of AAT protein, such as human subjects having AATD. In some embodiments, the methods include administering an AAT RNAi agent that is linked to a targeting group or targeting ligand as described herein, to a subject in need of treatment. In some embodiments, one or more pharmaceutically acceptable excipients (including vehicles, carriers, diluents, and/or delivery polymers) are added to the pharmaceutical compositions that include an AAT RNAi agent, thereby forming a pharmaceutical formulation suitable for in vivo delivery to a human subject.

The pharmaceutical compositions that include an AAT RNAi agent, when administered to a human subject using the methods disclosed herein, decrease the level of AAT mRNA in the subject.

In some embodiments, the described pharmaceutical compositions including an AAT RNAi agent are used for treating or managing clinical presentations in a subject with AATD, such as chronic hepatitis, cirrhosis, increased risk of hepatocellular carcinoma, transaminitis, cholestasis, fibrosis, and even fulminant hepatic failure. In some embodiments, a therapeutically or prophylactically effective amount of one or more of pharmaceutical compositions is administered to a subject in need of such treatment. In some embodiments, administration of any of the disclosed AAT RNAi agents can be used to decrease the number, severity, and/or frequency of symptoms of a disease in a subject.

The described pharmaceutical compositions that include an AAT RNAi agent can be used to treat at least one symptom in a subject having a disease or disorder that would benefit from reduction or inhibition in expression of AAT mRNA. In some embodiments, the subject is administered a therapeutically effective amount of one or more pharmaceutical compositions including an AAT RNAi agent thereby treating the symptom. In other embodiments, the subject is administered a prophylactically effective amount of one or more AAT RNAi agents, thereby preventing the at least one symptom.

The AAT RNAi agents disclosed herein can be administered via any suitable route in a preparation appropriately tailored to the particular route. Thus, herein described pharmaceutical compositions can be administered by injection, for example, intravenously or subcutaneously. In some embodiments, the herein described pharmaceutical compositions are administered via subcutaneous injection.

As used herein, a pharmaceutical composition or medicament includes a pharmacologically effective amount of at least one AAT RNAi agents and one or more pharmaceutically acceptable excipients. Pharmaceutically acceptable excipients (excipients) are substances other than the Active Pharmaceutical Ingredient (API, therapeutic product, e.g., AAT RNAi agent) that are intentionally included in the drug delivery system. Excipients do not exert or are not intended to exert a therapeutic effect at the intended dosage. Excipients can act to a) aid in processing of the drug delivery system during manufacture, b) protect, support, or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients may include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble). For subcutaneous or intravenous administration, suitable carriers may include physiological saline, bacteriostatic water, Cremophor® ELTM (BASF. Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above.

In some embodiments, a pharmaceutical composition suitable for use in the methods disclosed herein includes the components identified in the Formulated AAT RNAi Drug Substance provided in Table 3, below.

The AAT RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. In some embodiments, the dosage unit is between about 5 mg and about 300 mg of AAT RNAi Drug Substance. In some embodiments, the dosage unit is between about 25 mg and about 200 mg of AAT RNAi Drug Substance. In some embodiments, the dosage unit is between about 100 mg and about 200 mg of AAT RNAi Drug Substance. In some embodiments, the dosage unit is about 100 mg of AAT RNAi Drug Substance. In some embodiments, the dosage unit is about 200 mg of AAT RNAi Drug Substance.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.).

As used herein, "pharmacologically effective amount," "therapeutically effective amount," or simply "effective amount" refers to that amount of an RNAi agent to produce a pharmacological, therapeutic or preventive result.

The described pharmaceutically acceptable formulations can be packaged into kits, containers, packs, or dispensers. The pharmaceutical compositions described herein can be packaged in pre-filled syringes or vials.

Formulated AAT RNAi Drug Substance

In some embodiments, the AAT RNAi Drug Substance as provided in Table 2 (ADS-001) is formulated with one or more pharmaceutically acceptable excipients to form a pharmaceutical composition suitable for administration to a human subject. In some embodiments, the AAT RNAi Drug Substance described in Table 2 is formulated at 230 mg/mL in an aqueous sodium phosphate buffer (0.5 mM sodium phosphate monobasic, 0.5 mM sodium phosphate dibasic), forming the Formulated AAT RNAi Drug Substance (ADS-001-1) shown in Table 3:

TABLE 3

Composition of Formulated AAT RNAi Drug Substance, per 1.0 mL

| Component | Function | Quality/Grade | Concentration |
|---|---|---|---|
| ADS-001 | Active ingredient | In-house | 230 mg |
| Sodium phosphate monobasic, monohydrate | Suspending agent | USP, Ph. Eur | 0.061 mg |
| Sodium phosphate dibasic, anhydrous | Suspending agent | USP, Ph, Eur | 0.062 mg |
| Water for injection (WFI) | Vehicle | USP, Ph. Eur | 879.2 mg |

The Formulated AAT RNAi Drug Substance according to Table 3 is prepared as a sterile formulation. In some embodiments, the Formulated AAT RNAi Drug Substance is packaged in a container, such as a glass vial. In some embodiments, the Formulated AAT RNAi Drug Substance is packaged in a glass vial with a fill volume of about 1.1 mL, and a desired volume for administration can be calculated based upon the desired dose level to be administered.

In some embodiments, the Formulated AAT RNAi Drug Substance set forth in Table 3 is administered to a human subject using the methods disclosed herein.

Human Subjects with AATD and AATD Diagnosis

The methods disclosed herein include treating alpha-1 antitrypsin deficiency (AATD) in a human subject in need thereof, including treatment of the symptoms and diseases caused by AATD in the human subject, using pharmaceutical compositions that include the AAT RNAi Drug Substance described in Table 2. In some embodiments, the human subject is diagnosed with AATD prior to administration. As noted herein, AATD is a genetic disorder caused by mutations in the gene transcript that results in translation of a mutant form of AAT protein, for which some mutant forms which are prone to abnormal folding lead to intracellular retention in hepatocytes. While various mutations of the SERPINA1 gene have been identified, the most common and serious form of AATD, the PiZZ genotype, is caused by a single base-pair substitution. In subjects with the PiZZ genotype, circulating AAT levels are often reported as less than 15% of levels in normal humans. In many cases, patients are initially diagnosed with COPD, asthma, or other lung disease without identification of the underlying cause. Over time, liver disease such as fibrosis and cirrhosis can develop due to the intercellular retention of the misfolded ("Z-AAT") protein and the inability to properly secrete the protein from liver cells. Pediatric patients typically present with clinical symptoms of liver disease, which may include asymptomatic chronic hepatitis, failure to thrive, poor feeding, or hepatomegaly and splenomegaly. AATD can be diagnosed and confirmed through standard genotyping of blood samples from the subject.

Dosing and Inhibition of AAT Gene Expression

Generally, an effective amount of an AAT RNAi agent will be in the range of from about 0.1 to about 10 mg/kg of body weight/day, e.g., from about 0.25 to about 5 mg/kg of body weight/day. In some embodiments, an effective amount of an AAT RNAi agent will be in the range of from about 0.5 to about 4 mg/kg of body weight per dose. In some embodiments, the effective amount is a fixed dose. In some embodiments, a fixed dose of between 5 mg to 300 mg of AAT RNAi Drug Substance is an effective dose. In some embodiments, a fixed dose of between 25 mg to 200 mg of AAT RNAi Drug Substance is an effective dose. The amount administered will likely depend on such variables as the overall age and health status of the patient, the relative biological efficacy of the compound delivered, the formulation of the drug, the presence and types of excipients in the formulation, and the route of administration. In some embodiments, a fixed dose of from about 10, 15, 20, 25, 30, 35, 40, 45, 50, 55, 60, 65, 70, 75, 80, 85, 90, 95, 100, 120, 140, 160, 180, 200, 220, 240, 260 or 280 mg to about 15, 20, 25, 30, 35, 40, 45, 50, 55, 60, 65, 70, 75, 80, 85, 90, 95, 100, 120, 140, 160, 180, 200, 220, 240, 260, 280 or 300 mg is an effective dose. In some embodiments, a fixed dose of about 25 mg, about 100 mg, or about 200 mg is an effective dose.

Also, it is to be understood that the initial dosage administered can, in some instances, be increased beyond the above upper level to rapidly achieve the desired blood-level or tissue level, or the initial dosage can, in some instances, be smaller than the optimum. For example, in some embodiments, an initial dose of from about 25 mg to about 200 mg of AAT RNAi Drug Substance is administered, followed by a second dose of from about 25 to 200 mg of AAT RNAi Drug Substance approximately 1 month later, and thereafter additional doses (a concept similar to "maintenance doses") are administered once every three months (i.e., once per quarter).

For treatment of disease or for formation of a medicament or composition for treatment of a disease, the pharmaceutical compositions described herein including an AAT RNAi agent can be combined with an excipient or with a second therapeutic agent or treatment including, but not limited to: a second or other RNAi agent, a small molecule drug, an antibody, an antibody fragment, peptide and/or aptamer.

In some embodiments, the gene expression level and/or mRNA level of an AAT gene in a subject to whom a described AAT RNAi agent is administered is reduced by at least about 5%, 10%, 15%, 20%, 25%, 30%, 35%, 40%, 45%, 50%, 55%, 60%, 65%, 70%, 75%, 80%, 85%, 95%, 96%, 97%, 98%, 99%, or greater than 99% relative to the subject prior to being administered the AAT RNAi agent or to a subject not receiving the AAT RNAi agent. The gene expression level and/or mRNA level in the subject is reduced in a cell, group of cells, and/or tissue of the subject.

In some embodiments, the protein level of AAT in a subject to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent. The protein level in the subject is reduced in a cell, group of cells, tissue, blood, and/or other fluid of the subject.

In some embodiments, the Z-AAT polymer protein level in a subject having AATD to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent. In some embodiments, the Z-AAT polymer protein level in a subject to whom a described AAT RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the AAT RNAi agent or to a subject not receiving the AAT RNAi agent.

A reduction in AAT gene expression, AAT mRNA, or AAT protein levels can be assessed and quantified by general methods known in the art. The Examples disclosed herein forth generally known methods for assessing inhibition of AAT gene expression and reduction in AAT protein levels. The reduction or decrease in AAT mRNA level and/or protein level (including Z-AAT polymer and/or monomer) are collectively referred to herein as a reduction or decrease in AAT or inhibiting or reducing the expression of AAT.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition of the number, severity, and/or frequency of one or more symptoms of a disease in a subject.

As used herein, "monthly dosing" or "monthly" administration means every 28 days. As used herein, "quarterly dosing" or "quarterly" administration means every 84 days. The term "about" when used in connection with monthly dosing means monthly dosing +/−3 days. The term "about" when used in connection with quarterly dosing means quarterly dosing +/−9 days.

As used herein, the phrase "introducing into a cell," when referring to an RNAi agent, means functionally delivering the RNAi agent into a cell. The phrase "functional delivery," means that delivering the RNAi agent to the cell in a manner that enables the RNAi agent to have the expected biological activity, e.g., sequence-specific inhibition of gene expression.

Unless stated otherwise, use of the symbol 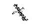 as used herein means that any group or groups may be linked thereto that is in accordance with the scope of the inventions described herein.

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The above provided embodiments and items are now illustrated with the following, non-limiting examples.

EXAMPLES

Example 1. Synthesis and Formulation of AAT RNAi Drug Substance (ADS-001)

The AAT RNAi Drug Substance suitable for use in the methods disclosed herein can be synthesized using standard phosphoramidite technology on solid phase oligonucleotide synthesis as is known in the art. Commercially available oligonucleotide synthesizers (e.g., MerMade96E®)(Bioautomation) or MerMade12® (Bioautomation)) may be used. Syntheses can be performed on a solid support made of controlled pore glass (CPG, 500 Å or 600 Å, obtained from Prime Synthesis, Aston, PA, USA). The monomer positioned at the 3' end of the respective strand may be attached to the solid support as a starting point for synthesis. All RNA, 2'-modified RNA phosphoramidites, and inverted abasic phosphoramidites can be purchased commercially. Targeting group-containing phosphoramidites can be synthesized that are suitable for addition to the 5' end of the sense strand. Standard cleavage, deprotection, purification, and annealing steps can be utilized as is known in the art. Further description related to the synthesis of AAT RNAi agents may be found, for example, in International Patent Application Publication No. WO 2018/132432 (Application No. PCT/US2018/013102) and WO 2018/044350 (PCT/US2017/021147), each of which is incorporated by reference herein in its entirety. AAT RNAi Drug Substance can then be formulated by dissolving in standard pharmaceutically acceptable excipients that are generally known in the art. For example, Table 3 shows a Formulated AAT RNAi Drug Substance that is suitable for use in the methods disclosed herein.

Example 2. Phase I Clinical Trial of AAT RNAi Drug Substance (ADS-001) in Normal Heathy Human Volunteers (NHV)

A Phase 1, single and multiple dose-escalating dose study to evaluate the safety, tolerability, pharmacokinetics and effect of AAT RNAi Drug Substance (ADS-001) on serum AAT levels in healthy volunteers (NHV) was conducted. The study subject population included healthy adult males and females 18-52 years old with a BMI between 19.0 and 35.0 kg/$m^2$.

NHV subjects were divided into a total of seven cohorts. Cohorts 1 through 4 were randomized to receive AAT RNAi Drug Substance or placebo (4 active: 4 placebo) at single escalating doses of 35 mg (Cohort 1) and multiple escalating doses of 100 mg (Cohort 2), 200 mg (Cohort 3) and 300 mg (Cohort 4) administered as a subcutaneous injection. Cohorts 1 through 4 were double-blinded. Cohorts 2b 3b and 4b were open label consisting of a subjects receiving single-doses of 100, 200, and 300 mg of AAT RNAi Drug Substance. A total of 44 subjects completed the study. FIG. 4 shows the final study design for the Phase I Clinical Trial. The study parameters are summarized in the following Table 4.

TABLE 4

| Phase I Clinical Study Parameters | |
|---|---|
| Development Phase | Phase 1: First-in-Human |
| Study Objectives | Primary Objectives:<br>To deteimine the incidence and frequency of adverse events possibly or probably related to treatment as a measure of the safety and tolerability of AAT RNAi Drug Substance (ADS-001) using escalating single doses and escalating multiple doses in normal healthy human volunteers (NHV).<br>Secondary Objectives:<br>To evaluate the single-dose and multi-dose pharmacokinetics of AAT RNAi. Drug Substance in NHV.<br>To determine the reduction in serum AAT in response to AAT RNAi Drug Substance as a measure of drug activity.<br>Exploratory Objectives:<br>To evaluate the effect of single doses of AAT RNAi Drug Substance on cytokines (Cytokine panel A: interleukin-6 [IL-6], monocyte chemoattractant protein-1 [MCP-1], tumor necrosis factor-alpha [TNF-alpha], interleukin-8 [IL-8], interleukin-1beta [IL-1beta], interferon alpha [IFN alpha], IL-10, IL-12 [p40], IL-12 [p70], macrophage inflammatory protein-1alpha [Mip-1alpha]) in NHV.<br>To evaluate the effect of single escalating doses of AAT RNAi Drug Substance on complement factors Bb, CH50, C5a, C4a, and C3a in NHV.<br>To collect plasma samples in NHV for subsequent metabolite identification (reported in a separate report outside of this study).<br>To collect urine samples in NHV for subsequent determination of urinary excretion and metabolite identification (reported in a separate report outside of this study). |

TABLE 4-continued

| Phase I Clinical Study Parameters | |
|---|---|
| Development Phase | Phase 1: First-in-Human |
| Study Design | Cohorts 1 through 4: randomized, double-blind, placebo-controlled<br>Cohorts 2b, 3b, and 4b: open label |
| Study Population | This study was conducted in MINTs, adult males and females, aged 18-52 years with BMI between 19.0 and 35.0 kg/$m^2$. |
| Investigational Product | AAT RNAi Drug Substance (ADS-001) (see Table 2), administered as Formulated AAT RNAi Drug Substance (see Table 3) |
| Dosage and Frequency | Cohort 1: randomized to receive AAT RNAi Drug Substance (ADS-001) or placebo (4 active: 4 placebo) at a single dose of 35 mg administered as a single subcutaneous injection.<br>Cohorts 2-4: randomized to receive three monthly (i.e., days 1, 29, and 57) doses of 100 mg (Cohort 2), 200 mg (Cohort 3), or 300 mg (Cohort 4) AAT RNAi Drug Substance or placebo (4 active: 4 placebo), via subcutaneous injection.<br>Cohorts 2b, 3b, and 4b: enrolled to receive a single dose of 100 mg (Cohort 2b), 200 mg (Cohort 3b), or 300 mg (Cohort 4b) AAT RNAi Drug Substance (4 active) administered as a single subcutaneous injection. |
| Reference Formulation | Placebo (PBO): normal saline (0.9%) administered subcutaneously with matching volume. |
| Safety Evaluation Criteria | Safety was assessed by adverse events, serious adverse events, physical examinations, vital sign measurements (blood pressure, heart rate, temperature, and respiratory rate), resting ECG measurements, clinical laboratory tests, concomitant medications/therapy, injection site reactions (ISRs), reasons for treatment discontinuation, and 90-day post-Day 29 (Cohort 1) and post-Day 113 (all other cohorts) pregnancy follow up. |
| Pharmacokinetics Evaluation | Blood samples will be collected from each subject for phatmacokinetic analysis after dose 1 (Cohort 1) and after dose 1 and 3 (Cohorts 2, 3, and 4) |
| Data Analysis | Screening, Compliance, Tolerability and Safety Data:<br>Safety analyses will be performed, and the results summarized by cohort. The incidence and frequency of adverse events (AEs), serious adverse events (SAEs), related AEs, related SAEs, and AEs leading to discontinuation, will be summarized by cohort per SOC, PT, and severity. Other safety parameters will be summarized at each scheduled time.<br>Phartnacokinetics (NHV subjects only):<br>Plasma concentrations of AAT RNAi Drug Substance constituents will be used to calculate the following PK parameters: maximum observed plasma concentration (Cmax), area under the plasma concentration time curve (AUC) from time 0 to 24 hours (AUC0-24), AUC front time 0 extrapolated to infinity (AUCinf), and terminal elimination half-life (t½), Pharmacokinetic parameters will be deter tined using non-compartmental methods. Descriptive statistics of PK parameters will include mean, standard deviation (SD), coefficient of variation, median, minimum, and maximum, PK results will be analyzed for dose proportionality, and sex differences. |

Serum AAT reduction results from the study showed that administration of AAT RNAi Drug Substance at doses from 35 to 300 mg resulted in deep reduction of serum AAT when compared with placebo. Initially, a cohort was proposed as part of the clinical trial protocol at 400 mg of AAT RNAi Drug Substance per dose. However, in view of the unexpected potency at the 35, 100, 200, and 300 mg doses, the 400 mg cohort was removed from the study protocol. Doses of 35 mg, 100 mg, and 200 mg yielded substantial serum AAT reductions, with both 100 mg and 200 mg reaching approximately 90% mean serum AAT reduction after multiple doses in the Phase I study. FIGS. 5 through 11 report on the serum AAT reductions of the various cohorts in the Phase I study.

There was no clear dose-dependent response across all dose levels because, surprisingly and unexpectedly, the dose levels at 100 mg and 200 mg produced substantial (reaching approximately 90%) and similar knockdown to the higher 300 mg dose. While the lowest dose of 35 mg was still quite active, it was not as active as 100 mg administered as a single dose, indicating a degree of dose response.

Duration of serum AAT reduction (>58%) from a single-dose of 35 mg lasted longer than initially anticipated, out to 16-weeks post dose administration with subsequent return towards baseline. For example, thirty-four weeks after the 35 mg single dose, one subject's serum AAT level has returned to above 90 mg/dL, while a second subject's serum AAT level remained at 40 mg/dL (60.4% reduced from baseline). There was no significant difference in the duration of response from single-doses of 100 mg to 300 mg of AAT RNAi Drug Substance, with return to baseline beginning between 8 and 16 weeks after the single-dose.

Multiple-doses of AAT RNAi Drug Substance maintain deep reduction in serum AAT for a longer duration than a single dose in general. These data suggest that a second dose received on Day 29 (i.e., after one month from an initial dose), may further reduce serum AAT levels or maintain reductions, and subsequent doses may be administered to maintain maximum reduced serum AAT every 12 weeks (i.e., quarterly).

In the Phase I study there were no deaths, no serious adverse events (SAEs), and no adverse events (AEs) rated as severe in intensity. Two subjects reported three AEs as moderate in intensity across subjects receiving AAT RNAi Drug Substance (upper respiratory tract infection, rhinorrhea, chest pain general). Three subjects reported three AEs as moderate in intensity across subjects receiving placebo (2-gastroenteritis, musculoskeletal chest pain-left sided). All other AEs have been reported as mild. The majority of subjects reported AEs not related to study treatment. One AE occurred in a subject receiving AAT which led to the premature discontinuation of therapy, although the subject continued to be followed on study. Ninety-four AEs were reported in 28 subjects receiving at least a single dose of Formulated AAT RNAi Drug Substance. Forty-six AEs were reported in 17 subjects receiving placebo. There is no clear pattern of an increased frequency or intensity of AEs with dose escalation.

Six AEs at the injection site occurred in 6 subjects across all Formulated AAT RNAi Drug Substance cohorts which all occurred in subjects receiving drug. There were no injection site AEs in placebo subjects. The injection site reactions reported included injection site bruising, erythema, and pain. These combined AEs at the injection site were reported by 21.4% of subjects receiving Formulated AAT RNAi Drug Substance. Six of 50 injections of Formulated AAT RNAi Drug Substance resulted in an injection site AE or 12%. No injection site AEs were reported more than once in a single subject. All injection site AEs have been considered mild in intensity.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating alpha-1 antitrypsin deficiency (AATD) in a human subject in need thereof, the method comprising administering by subcutaneous injection to the subject doses of a pharmaceutical composition comprising about 5 mg to about 300 mg of an AAT RNAi Drug Substance, wherein the AAT RNAi Drug Substance comprises:

a sense strand comprising the structure of (NAG37) s (invAb) sagcguuuaGfGfCfauguuuaacas (invAb) (SEQ ID NO:6) and an antisense strand comprising the structure of usGfsuUfaAfacaugCfcUfaAfaCfgCfsu (SEQ ID NO:2), wherein the sense and antisense strands are annealed to form a duplex, wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic deoxyribose residue; and (NAG37) s represents the structure of

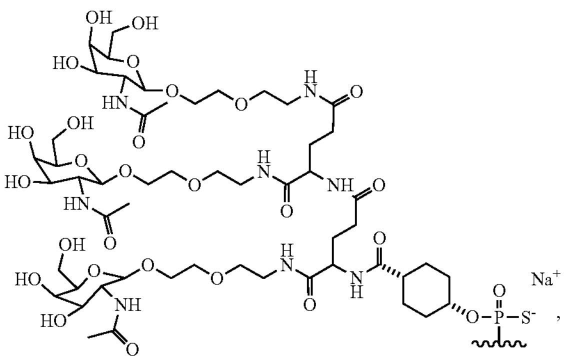

,

-continued

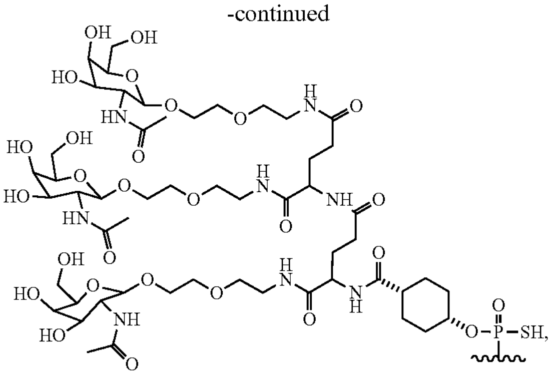

or both, wherein the pharmaceutical composition is administered once every 28 days.

2. A method of treating alpha-1 antitrypsin deficiency (AATD) in a human subject in need thereof, the method comprising administering by subcutaneous injection to the subject doses of a pharmaceutical composition comprising about 5 mg to about 300 mg of an AAT RNAi Drug Substance, wherein the AAT RNAi Drug Substance comprises:

a sense strand comprising the structure of (NAG37) s (invAb) sagcguuuaGfGfCfauguuuaacas (invAb) (SEQ ID NO:6) and an antisense strand comprising the structure of usGfsuUfaAfacaugCfcUfaAfaCfgCfsu (SEQ ID NO:2), wherein the sense and antisense strands are annealed to form a duplex, wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic deoxyribose residue; and (NAG37) s represents the structure of

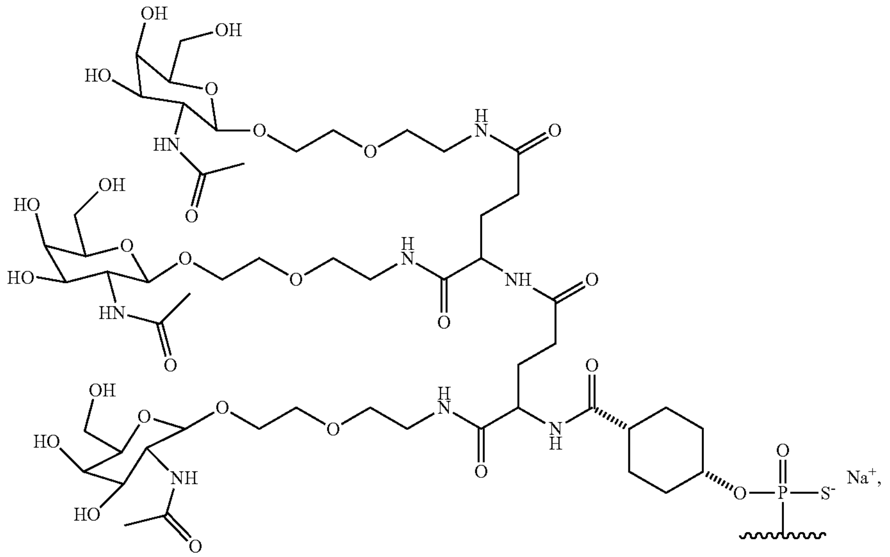

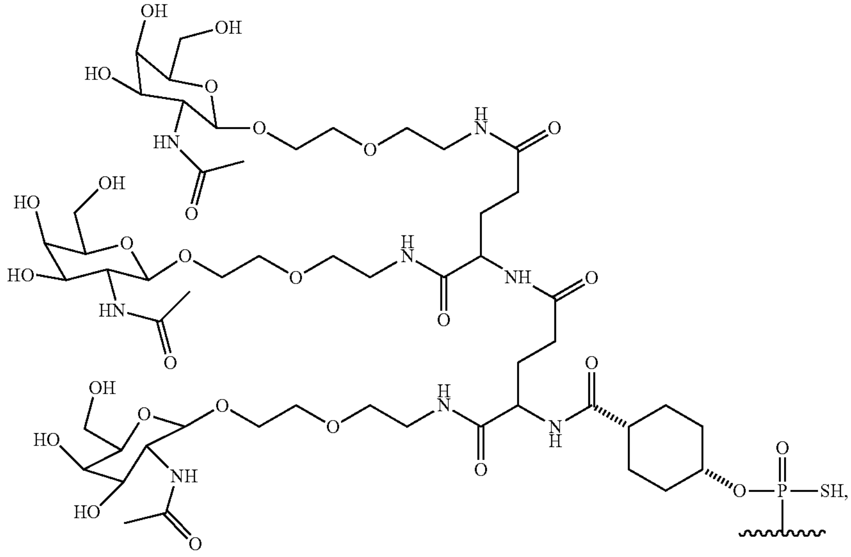

or both, wherein the pharmaceutical composition is administered once every 84 days.

3. A method of treating alpha-1 antitrypsin deficiency (AATD) in a human subject in need thereof, the method comprising administering to the subject by subcutaneous administration doses of a pharmaceutical composition comprising about 5 mg to about 300 mg of an AAT RNAi Drug Substance, wherein the AAT RNAi Drug Substance comprises:

a sense strand comprising the structure of (NAG37) s (invAb) sagcguuuaGfGfCfauguuuaacas (invAb) (SEQ ID NO:6) and an antisense strand comprising the structure of usGfsuUfaAfacaugCfcUfaAfaCfgCfsu (SEQ ID NO:2), wherein the sense and antisense strands are annealed to form a duplex, wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic deoxyribose residue; and (NAG37) s represents the structure of

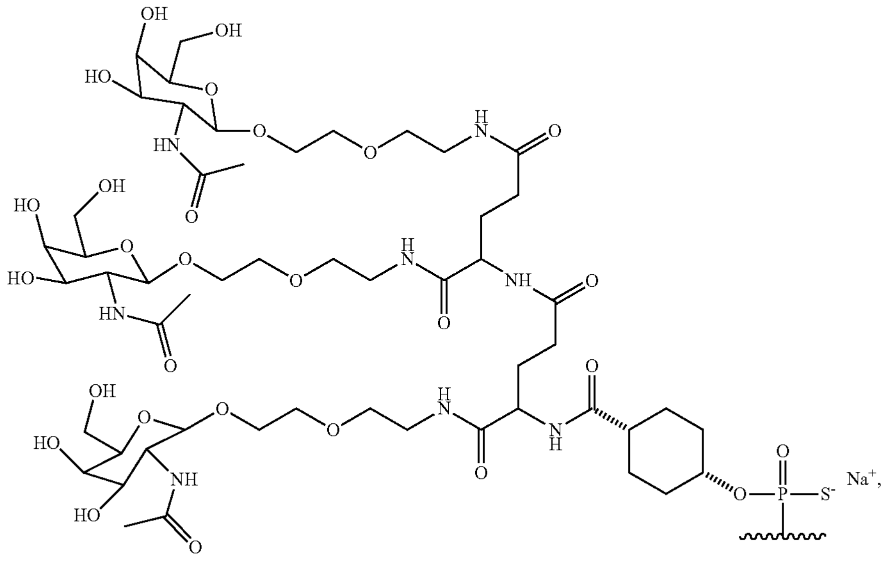

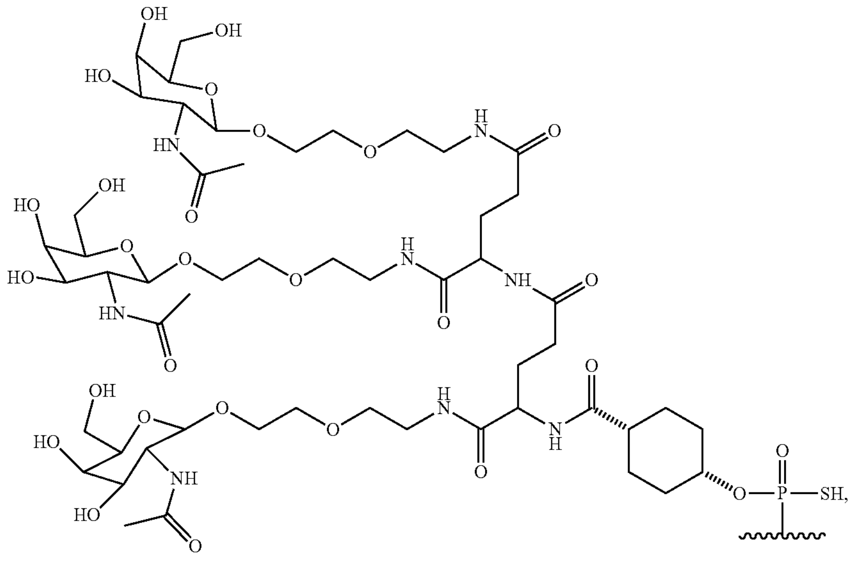

or both, wherein the administration comprises:

a. administering to the subject an initial dose of the pharmaceutical composition, b. administering to the subject a second dose of the pharmaceutical composition about 28 days after the initial dose, and c. administering to the subject a third dose of the pharmaceutical composition about 84 days after the second dose.

4. The method of claim 3, wherein each dose of the pharmaceutical composition comprises the AAT RNAi Drug Substance in an amount of about 25 mg to about 300 mg.

5. The method of claim 3, wherein each dose of the pharmaceutical composition comprises the AAT RNAi Drug Substance in an amount of about 100 mg to about 200 mg.

6. The method of claim 3, wherein each dose of the pharmaceutical composition comprises the AAT RNAi Drug Substance in an amount of about 25 mg.

7. The method of claim 3, wherein each dose of the pharmaceutical composition comprises the AAT RNAi Drug Substance in an amount of about 35 mg.

8. The method of claim 3, wherein each dose of the pharmaceutical composition comprises the AAT RNAi Drug Substance in an amount of about 100 mg.

9. The method of claim 3, wherein each dose of the pharmaceutical composition comprises the AAT RNAi Drug Substance in an amount of about 200 mg.

10. The method of claim 3, wherein each dose of the pharmaceutical composition comprises the AAT RNAi Drug Substance in an amount of about 180 mg to about 240 mg.

11. The method of claim 3, wherein the condition or disease caused by AATD is a liver disease.

12. The method of claim 11, wherein the liver disease is chronic hepatitis, cirrhosis, increased risk of hepatocellular carcinoma, transaminitis, cholestasis, fibrosis, or fulminant hepatic failure.

13. The method of claim 3, wherein the subject is further administered an additional therapeutic for the treatment of AATD.

14. The method of claim 3, wherein the subject is further administered a therapeutic for the treatment of lung damage, emphysema, or other lung diseases or disorders caused by the deficiency of endogenously secreted AAT protein.

15. The method of claim 14, wherein the additional therapeutic comprises human AAT protein, purified human alpha-1 proteinase inhibitor, or recombinant AAT protein.

16. The method of claim 3, wherein the pharmaceutical composition is packaged in a kit, container, pack, dispenser, pre-filled syringe, or vials.

17. The method of claim 3, wherein the pharmaceutical composition comprises, consists of, or consists essentially of the Formulated AAT RNAi Drug Substance comprising the AAT RNAi Drug Substance formulated at 230 mg/mL in an aqueous sodium phosphate buffer of 0.5 mM sodium phosphate monobasic and 0.5 mM sodium phosphate dibasic.

18. The method of claim 3, further comprising administering additional doses after the third dose, wherein the additional doses are administered about 84 days apart.

19. The method of claim 3, wherein the administration of one or more doses of the pharmaceutical composition is performed by the subject.

20. The method of claim 3, wherein the administration of one or more doses of the pharmaceutical composition is performed by a medical professional.

21. A method of treating alpha-1 antitrypsin deficiency (AATD) in a human subject in need thereof, the method comprising administering to the subject by subcutaneous administration doses of a pharmaceutical composition comprising about 200 mg of an AAT RNAi Drug Substance, wherein the AAT RNAi Drug Substance comprises:

a sense strand comprising the structure of (NAG37) s (invAb) sagcguuuaGfGfCfauguuuaacas (invAb) (SEQ ID NO:6) and an antisense strand comprising the structure of usGfsuUfaAfacaugCfcUfaAfaCfgCfsu (SEQ ID NO:2), wherein the sense and antisense strands are annealed to form a duplex, wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; (invAb) represents an inverted abasic deoxyribose residue; and (NAG37) s represents the structure of

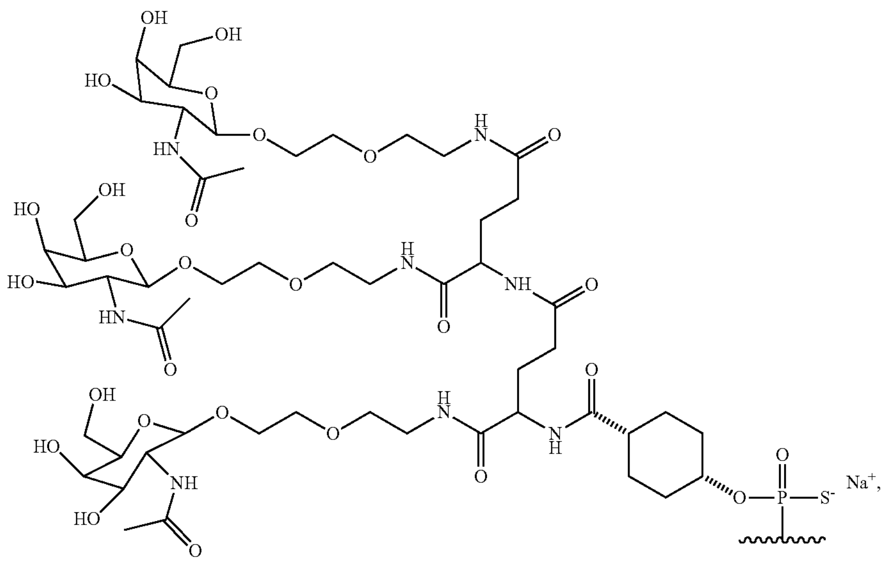

,

-continued

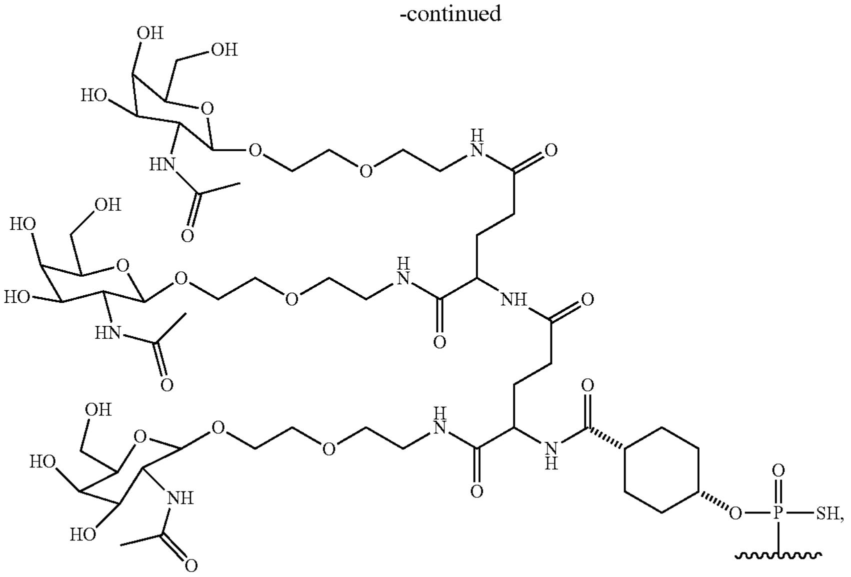

or both, wherein the administration comprises:

a. administering to the subject an initial dose of the pharmaceutical composition, b. administering to the subject a second dose of the pharmaceutical composition comprising about 28 days after the initial dose, and c. administering to the subject a third dose of the pharmaceutical composition comprising about 84 days after the second dose.

22. The method of claim 21, further comprising administering additional doses after the third dose, wherein the additional doses are administered about 84 days apart.

* * * * *

SEQUENCE LISTING

```
<160> NUMBER OF SEQ ID NOS: 6

<210> SEQ ID NO 1
<211> LENGTH: 3220
<212> TYPE: DNA
<213> ORGANISM: Homo sapiens
<220> FEATURE:
<223> OTHER INFORMATION: Homo sapiens serpin family A member 1
      (SERPINA1), gene transcript variant 1 (NM_000295.4)

<400> SEQUENCE: 1

acaatgactc ctttcggtaa gtgcagtgga agctgtacac tgcccaggca aagcgtccgg     60

gcagcgtagg cgggcgactc agatcccagc cagtggactt agcccctgtt tgctcctccg    120

ataactgggg tgaccttggt taatattcac cagcagcctc ccccgttgcc cctctggatc    180

cactgcttaa atacggacga ggacagggcc ctgtctcctc agcttcaggc accaccactg    240

acctgggaca gtgaatcgac aatgccgtct tctgtctcgt ggggcatcct cctgctggca    300

ggcctgtgct gcctggtccc tgtctccctg gctgaggatc cccagggaga tgctgcccag    360

aagacagata catcccacca tgatcaggat cacccaacct tcaacaagat cacccccaac    420

ctggctgagt tcgccttcag cctataccgc cagctggcac accagtccaa cagcaccaat    480

atcttcttct ccccagtgag catcgctaca gcctttgcaa tgctctccct ggggaccaag    540

gctgacactc acgatgaaat cctggagggc ctgaatttca acctcacgga gattccggag    600

gctcagatcc atgaaggctt ccaggaactc ctccgtaccc tcaaccagcc agacagccag    660

ctccagctga ccaccggcaa tggcctgttc ctcagcgagg gcctgaagct agtggataag    720

tttttggagg atgttaaaaa gttgtaccac tcagaagcct tcactgtcaa cttcggggac    780

accgaagagg ccaagaaaca gatcaacgat tacgtggaga agggtactca agggaaaatt    840

gtggatttgg tcaaggagct tgacagagac acagtttttg ctctggtgaa ttacatcttc    900

tttaaaggca aatgggagag accctttgaa gtcaaggaca ccgaggaaga ggacttccac    960

gtggaccagg tgaccaccgt gaaggtgcct atgatgaagc gtttaggcat gtttaacatc   1020

cagcactgta agaagctgtc cagctgggtg ctgctgatga aatacctggg caatgccacc   1080

gccatcttct tcctgcctga tgaggggaaa ctacagcacc tggaaaatga actcacccac   1140
```

-continued

```
gatatcatca ccaagttcct ggaaaatgaa gacagaaggt ctgccagctt acatttaccc   1200
aaactgtcca ttactggaac ctatgatctg aagagcgtcc tgggtcaact gggcatcact   1260
aaggtcttca gcaatggggc tgacctctcc ggggtcacag aggaggcacc cctgaagctc   1320
tccaaggccg tgcataaggc tgtgctgacc atcgacgaga aagggactga agctgctggg   1380
gccatgtttt tagaggccat acccatgtct atcccccccg aggtcaagtt caacaaaccc   1440
tttgtcttct taatgattga acaaaatacc aagtctcccc tcttcatggg aaaagtggtg   1500
aatcccaccc aaaaataact gcctctcgct cctcaacccc tcccctccat ccctggcccc   1560
ctccctggat gacattaaag aagggttgag ctggtccctg cctgcatgtg actgtaaatc   1620
cctcccatgt tttctctgag tctccctttg cctgctgagg ctgtatgtgg gctccaggta   1680
acagtgctgt cttcgggccc cctgaactgt gttcatggag catctggctg ggtaggcaca   1740
tgctgggctt gaatccaggg ggactgaat cctcagctta cggacctggg cccatctgtt   1800
tctggagggc tccagtcttc cttgtcctgt cttggagtcc ccaagaagga atcacagggg   1860
aggaaccaga taccagccat gaccccaggc tccaccaagc atcttcatgt ccccctgctc   1920
atcccccact cccccccacc cagagttgct catcctgcca gggctggctg tgcccacccc   1980
aaggctgccc tcctgggggc cccagaactg cctgatcgtg ccgtggccca gttttgtggc   2040
atctgcagca acacaagaga gaggacaatg tcctcctctt gacccgctgt cacctaacca   2100
gactcgggcc ctgcacctct caggcacttc tggaaaatga ctgaggcaga ttcttcctga   2160
agcccattct ccatggggca acaaggacac ctattctgtc cttgtccttc catcgctgcc   2220
ccagaaagcc tcacatatct ccgtttagaa tcaggtccct tctccccaga tgaagaggag   2280
ggtctctgct ttgttttctc tatctcctcc tcagacttga ccaggcccag caggccccag   2340
aagaccatta ccctatatcc cttctcctcc ctagtcacat ggccataggc ctgctgatgg   2400
ctcaggaagg ccattgcaag gactcctcag ctatgggaga ggaagcacat cacccattga   2460
cccccgcaac ccctcccttt cctcctctga gtcccgactg gggccacatg cagcctgact   2520
tctttgtgcc tgttgctgtc cctgcagtct tcagagggcc accgcagctc cagtgccacg   2580
gcaggaggct gttcctgaat agcccctgtg gtaagggcca ggagagtcct tccatcctcc   2640
aaggccctgc taaaggacac agcagccagg aagtcccctg ggcccctagc tgaaggacag   2700
cctgctccct ccgtctctac caggaatggc cttgtcctat ggaaggcact gccccatccc   2760
aaactaatct aggaatcact gtctaaccac tcactgtcat gaatgtgtac ttaaaggatg   2820
aggttgagtc ataccaaata gtgatttcga tagttcaaaa tggtgaaatt agcaattcta   2880
catgattcag tctaatcaat ggataccgac tgtttcccac acaagtctcc tgttctctta   2940
agcttactca ctgacagcct ttcactctcc acaaatacat taaagatatg gccatcacca   3000
agccccctag gatgacacca gacctgagag tctgaagacc tggatccaag ttctgacttt   3060
tcccccctgac agctgtgtga ccttcgtgaa gtcgccaaac ctctctgagc cccagtcatt   3120
gctagtaaga cctgcctttg agttggtatg atgttcaagt tagataacaa aatgtttata   3180
cccattagaa cagagaataa atagaactac atttcttgca                         3220
```

<210> SEQ ID NO 2
<211> LENGTH: 21
<212> TYPE: RNA
<213> ORGANISM: Artificial sequence
<220> FEATURE:
<223> OTHER INFORMATION: AAT RNAi agent antisense strand modified sequence -continued

<400> SEQUENCE: 2
uguuaaacau gccuaaacgc u 21

<210> SEQ ID NO 3
<211> LENGTH: 21
<212> TYPE: RNA
<213> ORGANISM: Artificial sequence
<220> FEATURE:
<223> OTHER INFORMATION: AAT RNAi agent antisense strand underlying base sequence

<400> SEQUENCE: 3
uguuaaacau gccuaaacgc u 21

<210> SEQ ID NO 4
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 4
agcguuuagg cauguuuaac a 21

<210> SEQ ID NO 5
<211> LENGTH: 21
<212> TYPE: RNA
<213> ORGANISM: Artificial sequence
<220> FEATURE:
<223> OTHER INFORMATION: AAT RNAi agent sense strand underlying base sequence

<400> SEQUENCE: 5
agaugcugcc cagaagacac a 21

<210> SEQ ID NO 6
<211> LENGTH: 21
<212> TYPE: RNA
<213> ORGANISM: Artificial sequence
<220> FEATURE:
<223> OTHER INFORMATION: AAT RNAi agent sense strand modified sequence

<400> SEQUENCE: 6
agcguuuagg cauguuuaac a 21